United States Patent
Paterson

(10) Patent No.: US 7,774,182 B2
(45) Date of Patent: Aug. 10, 2010

(54) APPARATUS AND METHOD FOR VALIDATING A COMPUTER MODEL

(75) Inventor: Thomas Paterson, Redondo Beach, CA (US)

(73) Assignee: Entelos, Inc., Foster City, CA (US)

( * ) Notice: Subject to any disclaimer, the term of this patent is extended or adjusted under 35 U.S.C. 154(b) by 0 days.

(21) Appl. No.: 12/208,141

(22) Filed: Sep. 10, 2008

(65) Prior Publication Data

US 2009/0132219 A1    May 21, 2009

Related U.S. Application Data

(63) Continuation of application No. 10/151,581, filed on May 16, 2002, now abandoned.

(60) Provisional application No. 60/292,175, filed on May 17, 2001.

(51) Int. Cl.
*G06F 17/10* (2006.01)

(52) U.S. Cl. .............................. 703/6; 703/2

(58) Field of Classification Search ............ 703/2, 703/11, 6
See application file for complete search history.

(56) References Cited

U.S. PATENT DOCUMENTS

| | | |
|---|---|---|
| 3,955,290 A | 5/1976 | Filer |
| 4,015,343 A | 4/1977 | Gottsdanker |
| 4,066,882 A | 1/1978 | Esposito |
| 5,428,740 A | 6/1995 | Wood et al. |
| 5,446,652 A | 8/1995 | Peterson et al. |
| 5,657,255 A | 8/1997 | Fink et al. |
| 5,780,164 A | 7/1998 | Pyzik et al. |
| 5,808,918 A | 9/1998 | Fink et al. |
| 5,840,020 A | 11/1998 | Heinonen et al. |
| 5,914,891 A | 6/1999 | McAdams et al. |
| 5,921,920 A | 7/1999 | Marshall et al. |
| 5,947,899 A | 9/1999 | Winslow et al. |

(Continued)

FOREIGN PATENT DOCUMENTS

WO    96/08781 A1    3/1996

(Continued)

OTHER PUBLICATIONS

John Wahren, et al., "Glucose Metabolism During Leg Exercise in Man," The Journal of Clinical Investigation, 1971, pp. 2715-2725, vol. 50.

(Continued)

*Primary Examiner*—Paul L Rodriguez
*Assistant Examiner*—Luke Osborne
(74) *Attorney, Agent, or Firm*—Karen E. Flick

(57) ABSTRACT

An apparatus and method for validating a computer model is described. In one embodiment, a computer-readable medium comprises instructions to associate a set of configurations of a computer model with a stimulus-response test, each configuration of the set of configurations representing a different model scenario, the stimulus-response test defining a modification to each configuration of the set of configurations. The computer-readable medium also comprises instructions to apply the stimulus-response test to the set of configurations to produce a simulated response for each configuration of the set of configurations and instructions to compare the simulated responses for the set of configurations with an expected response to the stimulus-response test.

4 Claims, 14 Drawing Sheets

U.S. PATENT DOCUMENTS

| | | |
|---|---|---|
| 6,051,029 A | 4/2000 | Paterson et al. |
| 6,069,629 A | 5/2000 | Paterson et al. |
| 6,078,739 A | 6/2000 | Paterson et al. |
| 6,108,635 A | 8/2000 | Herren et al. |
| 6,983,237 B2 | 1/2006 | Paterson et al. |
| 7,353,152 B2 | 4/2008 | Brazhnik et al. |
| 2001/0032068 A1 | 10/2001 | Paterson et al. |
| 2002/0091666 A1 | 7/2002 | Rice et al. |
| 2003/0009099 A1 | 1/2003 | Lett et al. |
| 2003/0018457 A1 | 1/2003 | Lett et al. |
| 2003/0033127 A1 | 2/2003 | Lett |

FOREIGN PATENT DOCUMENTS

| | | |
|---|---|---|
| WO | 98/20437 A2 | 5/1998 |
| WO | 98/20459 A1 | 5/1998 |
| WO | 99/23554 A1 | 5/1999 |
| WO | 99/27443 A1 | 6/1999 |
| WO | 99/27444 A1 | 6/1999 |
| WO | 00/32258 A1 | 6/2000 |
| WO | 00/63793 A2 | 10/2000 |
| WO | 00/65523 A1 | 11/2000 |
| WO | 01/57775 A2 | 8/2001 |
| WO | 01/98935 A2 | 12/2001 |
| WO | 02/44992 A2 | 6/2002 |

OTHER PUBLICATIONS

C. Cobelli, et al. "An Integrated Mathematical Model of the Dynamics of Blood Glucose and Its Hormonal Control," Mathematical Biosciences, 1982, pp. 27-60, vol. 58.

P. Mendes, et al. "Non-Linear Optimization of Biochemical Pathways: Applications to Metabolic Engineering and Parameter Estimation," Bioinformatics, 1998, pp. 869-883, vol. 14, No. 10.

J. S. Edwards, et al., The *Escherichia coli* MG1655 in Silico Metabolic Genotype: Its Definition, Characteristics, and Capabilities, PNAS, May 9, 2000, pp. 5528-5533, vol. 97, No. 10.

J. S. Edwards, et al., Metabolic Flux Balance Analysis and the in Silico Analysis of *Es-cherichia coli* K-12 Gene Deletions, BMC Bioinformatics, Jul. 27, 2000, pp. 10, vol. 1, No. 1.

J. S. Edwards, et al., "In Silico Predictions of *Escherichia coli* Metabolic Capabilities are Consistent with Experimental Data," Nature Biotechnology, Feb. 2001, pp. 125-130, vol. 19, No. 2.

J. S. Edwards, et al., "Characterizing the Metabolic Phenotype: A Phenotype Phase Plane Analysis," Biotechnology and Bioengineering, Jan. 5, 2002, pp. 27-36, vol. 77, No. 1.

F. Hynne, et al., "Full-Scale Model of Glycolysis in *Saccharomyces cerevisiae*," Biophysical Chemistry, 2001, pp. 121-163, vol. 94.

Robert G. Sargent, "Verification, Validation and Accreditation of Simulation Models", 2000, Proceedings of the 2000 Winter Simulation Conference, ACM, pp. 50-59.

Jessop, et al. Atlas—an automated software testing system.: 2nd International Conference on Software Engineering IEEE, New York, NY, USA, 1976, pp. 629-635.

APPARATUS AND METHOD FOR VALIDATING A COMPUTER MODEL

CROSS REFERENCE TO RELATED APPLICATION

This application claims the benefit of U.S. Provisional Application Ser. No. 60/292,175, entitled "Developing, Analyzing, and Validating a Computer-Based Model" and filed on May 17, 2001, the disclosure of which is incorporated herein by reference in its entirety.

COPYRIGHT NOTICE

A portion of the disclosure of the patent document contains material that is subject to copyright protection. The copyright owner has no objection to the facsimile reproduction by anyone of the patent document, as it appears in the Patent and Trademark Office patent file or records, but otherwise reserves all copyright rights whatsoever.

FIELD OF THE INVENTION

The present invention relates generally to computer models. More particularly, the present invention relates to validation of computer models.

BACKGROUND OF THE INVENTION

Validation is generally a key aspect of developing and utilizing a computer model. Validation typically refers to a process of establishing a certain level of confidence that a computer model will behave as expected when compared to actual, predicted, or desired data for a modeled system. Once the computer model has been validated, additional analysis to gain further understanding of the modeled system is a logical next step.

Previous attempts for validating a computer model typically involved a manual process of specifying various conditions for the computer model and evaluating behavior of the computer model for the various conditions. Particularly when validating complex computer models, such manual process can be tedious, time-consuming, and prone to errors or inconsistencies. At the same time, some of the previous attempts are not sensitive to different configurations of a computer model and, therefore, cannot provide full validation capabilities.

In addition, validation of computer models for certain modeled systems can pose significant challenges. In particular, the behavior of certain modeled systems may be understood at a higher or aggregate level but may be poorly understood at a lower level. Accordingly, a "bottom-up" framework, as traditionally used, is typically inadequate for validating computer models of such modeled systems.

It is against this background that a need arose to develop the apparatus and method described herein.

SUMMARY OF THE INVENTION

In one innovative aspect, the present invention relates to a computer-readable medium. In one embodiment, the computer-readable medium comprises instructions to associate a set of configurations of a computer model with a stimulus-response test, each configuration of the set of configurations representing a different model scenario, the stimulus-response test defining a modification to each configuration of the set of configurations. The computer-readable medium also comprises instructions to apply the stimulus-response test to the set of configurations to produce a simulated response for each configuration of the set of configurations and instructions to compare the simulated responses for the set of configurations with an expected response to the stimulus-response test.

BRIEF DESCRIPTION OF THE DRAWINGS

For a better understanding of the nature and objects of the present invention, reference should be made to the following detailed description taken in conjunction with the accompanying drawings, in which:

FIG. 5 illustrates an example of a user-interface screen indicating a virtual patient that is created based on a baseline virtual patient.

FIG. 15 illustrates an example of a user-interface screen indicating patient response types that can be selected and associated with a given virtual patient.

DETAILED DESCRIPTION OF THE INVENTION

Overview

Figure 1:
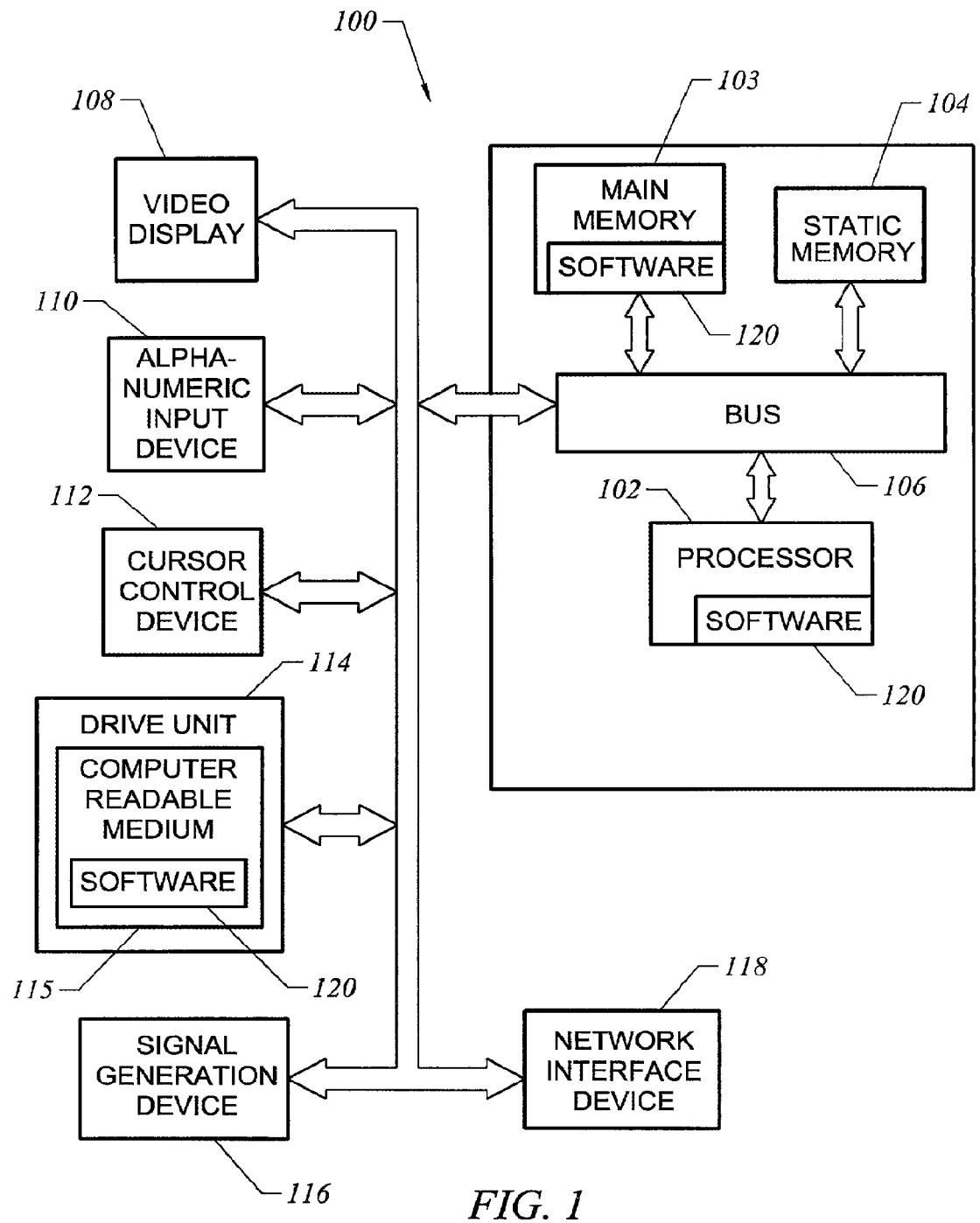
FIG. 1 illustrates a system block diagram of a computer that can be operated in accordance with some embodiments of the invention.

FIG. 1 illustrates a system block diagram of a computer 100 that can be operated in accordance with some embodiments of the invention. The computer 100 includes a processor 102, a main memory 103, and a static memory 104, which are coupled by bus 106. The computer 100 can also include a video display unit 108 (e.g., a liquid crystal display (LCD) or a cathode ray tube (CRT)) display) on which a user-interface can be displayed. The computer 100 can further include an alpha-numeric input device 110 (e.g., a keyboard), a cursor control device 112 (e.g., a mouse), a disk drive unit 114, a signal generation device 116 (e.g., a speaker), and a network interface device 118. The disk drive unit 114 includes a computer-readable medium 115 storing software instructions 120 that implement processing according to some embodiments of the invention. As used herein, the term "computer-readable medium" can include any medium which is capable of storing or encoding a sequence of instructions for performing the processing described herein and can include, but is not limited to, optical storage devices, magnetic storage devices, disks, carrier waves signals, or a combination thereof. The software instructions 120 can reside within the main memory 103, the processor 102, or both. For certain applications, the software instructions 120 can be transmitted or received via the network interface device 118.

Figure 2:
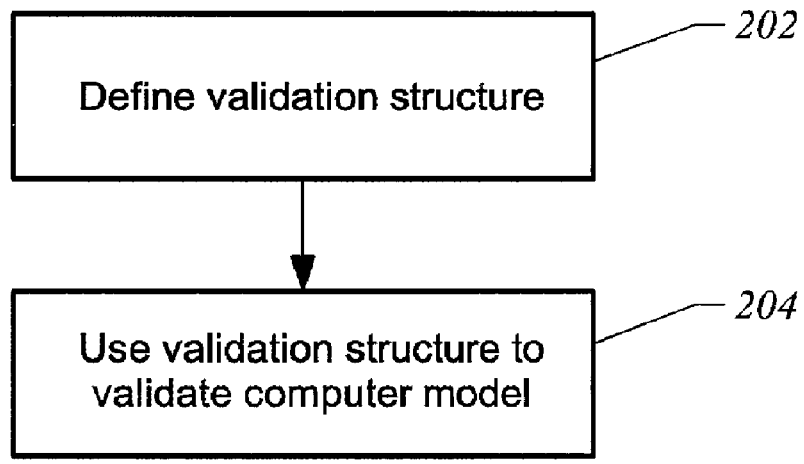
FIG. 2 illustrates a flow chart to validate a computer model in accordance with an embodiment of the invention.

FIG. 2 illustrates a flow chart to validate a computer model in accordance with an embodiment of the invention. The computer model to be validated can represent any of a variety of modeled systems that may be of interest to a user. Typically, a modeled system will be based on a real-world system. By way of example, the modeled system can be a biological system (e.g., a cell, tissue, organ, multi-cellular organism, or population of cellular or multi-cellular organisms), a chemical system (e.g., a chemical reaction), an ecosystem (e.g., a predator-prey ecosystem), an electrical system (e.g., an electric circuit), an environmental system (e.g., atmospheric level of a pollutant), a financial system (e.g., a stock market), or a mechanical system (e.g., a motor).

The first step shown in FIG. 2 is to define a validation structure to validate the computer model (step 202). In the present embodiment of the invention, the validation structure includes a set (i.e., one or more) of stimulus-response tests. A stimulus-response test can be defined to simulate a stimulus or perturbation that can be applied to the modeled system. In particular, the stimulus-response test can define a modification to the computer model to simulate the stimulus. The validation structure can also include a set of expected responses associated with the set of stimulus-response tests. In particular, each stimulus-response test can be associated with one or more expected responses to the stimulus-response test. An expected response to a stimulus-response test can be based on actual, predicted, or desired behavior of the modeled system when subjected to a stimulus simulated by the stimulus-response test.

The second step shown in FIG. 2 is to use the validation structure to validate the computer model (step 204). In the present embodiment of the invention, the computer model is associated with one or more stimulus-response tests of the set of stimulus-response tests, and the one or more stimulus-response tests are applied to the computer model to produce a simulated response to each stimulus-response test. More particularly, the one or more stimulus-response tests can be automatically applied to the computer model to produce one or more simulated responses. Once produced, a simulated response to a stimulus-response test can be displayed for a user. Alternatively, or in conjunction, a simulated response to a stimulus-response test can be compared with an expected response to the stimulus-response test. The computer model can be validated if one or more simulated responses sufficiently conform to one or more expected responses.

Computer Model

Figure 3:
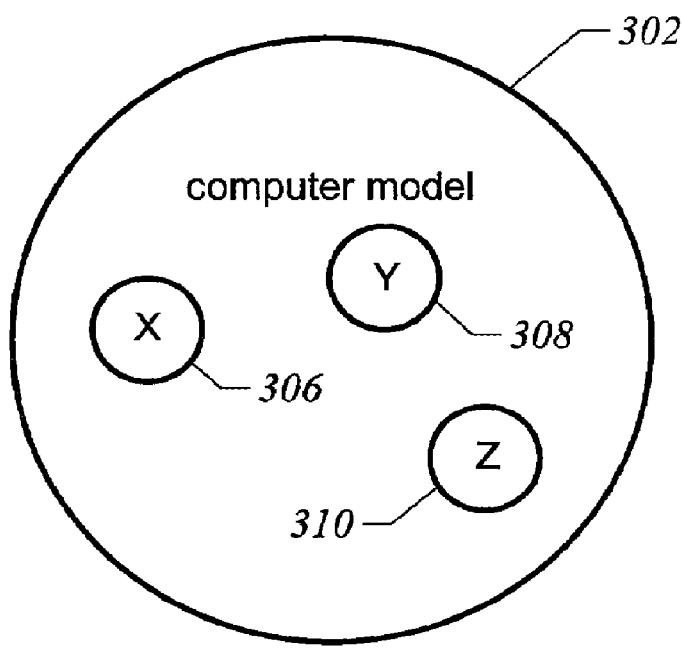
FIG. 3 illustrates the architecture of a computer model that can be validated in accordance with an embodiment of the invention.

FIG. 3 illustrates the architecture of a computer model 302 that can be validated in accordance with an embodiment of the invention. As discussed previously, the computer model 302 can represent any of a variety of modeled systems that may be of interest to a user.

The computer model 302 may be defined as, for example, described in the patent to Paterson et al., entitled "Method of Managing Objects and Parameter Values Associated with the Objects Within a Simulation Model", U.S. Pat. No. 6,078,739, issued on Jun. 20, 2000; the patent to Fink et al., entitled "Hierarchical Biological Modelling System and Method", U.S. Pat. No. 5,657,255, issued on Aug. 12, 1997; and the co-owned and co-pending patent application to Brazhnik et al., entitled "Method and Apparatus for Computer Modeling Diabetes", U.S. application Ser. No. 10/040,373, filed on Jan. 9, 2002; the disclosures of which are incorporated herein by reference in their entirety. Alternatively, or in conjunction, the computer model 302 may be defined as in commercially available computer models such as, for example, Entelos® Asthma PhysioLab® systems, Entelos® Obesity PhysioLab® systems, and Entelos® Adipocyte CytoLab® systems.

In the present embodiment of the invention, the computer model 302 can be a mathematical model that represents a set of dynamic processes associated with a modeled system using a set of mathematical relations. A mathematical relation typically includes one or more variables, each of which represents a quantity for which the behavior (e.g., time evolution) can be simulated by the computer model 302. The behavior of variables may be influenced by a set of parameters included in the computer model 302. For example, parameters can include initial values of variables, half-lives of variables, rate constants, conversion ratios, exponents, and curve-fitting parameters. One or more parameters may be included in the mathematical relations of the computer model 302.

The mathematical relations employed in the computer model 302 may include, for example, ordinary differential equations, partial differential equations, stochastic differential equations, differential algebraic equations, difference equations, cellular automata, coupled maps, equations of networks of Boolean, fuzzy logical networks, or a combination thereof. For certain applications, the mathematical relations used in the computer model 302 are ordinary differential equations that may take the form:

$$dx/dt = f(x, p, t),$$

where x is an N dimensional set of variables, t is time, dx/dt is the rate of change of x, p is an M dimensional set of parameters, and f is a function that represents interactions among the variables.

For certain applications, the computer model 302 can be configured to allow visual representation of the mathematical relations as well as interrelationships between variables, parameters, and processes. This visual representation can include multiple modules or functional areas that, when grouped together, represent a large complex model of the modeled system.

In the present embodiment of the invention, the computer model 302 can be configured to simulate behavior of variables by, for example, numerical or analytical integration of one or more mathematical relations. For example, numerical integration of the ordinary differential equations defined above can be performed to obtain values for the variables at various times.

By way of example, if the modeled system is a biological system, the computer model 302 can represent one or more processes (e.g., one or more biological processes) associated with the biological system using one or more mathematical relations. For instance, the computer model 302 can represent a first biological process using a first mathematical relation and a second biological process using a second mathematical relation. For example, biological processes can include digestion, absorption, storage, and oxidation of carbohydrate, fat, and protein, as well as the endocrine control of these processes. The mathematical relations can define interactions among variables (e.g., biological variables), where the biological variables can represent quantities associated with inter-cellular constituents, cellular constituents, intra-cellular constituents, or a combination thereof, that make up the biological system. Constituents can include, for example, metabolites; DNA; RNA; proteins; enzymes; hormones; cells; organs; tissues; portions of cells, tissues, or organs; subcellular organelles; chemically reactive molecules like $H^+$; superoxides; ATP; citric acid; protein albumin; as well as combinations or aggregate representations of these constituents. The biological variables can represent, for example, levels or concentrations of constituents such as plasma glucose, insulin, free fatty acids, and so forth. The behavior of one or more biological variables typically will be affected by one or more parameters included in the computer model 302. One or more parameters can be used to specify intrinsic properties (e.g., genetic factors or susceptibilities) as well as external influences (e.g., environmental factors) for the biological system. Parameters can correlate to, for example, initial body weight, basal muscle glucose uptake rate, level of physical activity, nutrient composition of diet, food intake, level of intestinal signaling, level of insulin resistance, and so forth.

In the present embodiment of the invention, the computer model 302 includes one or more configurations. With reference to FIG. 3, the computer model 302 is shown including configuration X 306, configuration Y 308, and configuration Z 310. The various configurations of the computer model 302 can represent different model scenarios. Different model scenarios can correlate to, for example, different variations of the modeled system having different intrinsic properties, different external influences, or both.

By way of example, the modeled system represented by the computer model 302 can be a biological system. The observable condition (e.g., an outward manifestation) of the biological system can be referred to as its phenotype, while the underlying conditions of the biological system that give rise to the phenotype can be based on genetic factors, environmental factors, or both. As one of ordinary skill in the art will understand, phenotypes of a biological system can be defined with varying degrees of specificity. For instance, a phenotype (e.g., a disease phenotype) may be generally defined as an overweight condition or may be more specifically defined as a severely overweight condition (e.g., 90 kg or more for a human patient). A given phenotype typically can be reproduced by different underlying conditions (e.g., different combination of genetic and environmental factors). For example, two individuals may appear to be similarly overweight, but one could be overweight because of genetic factors, while the other could be overweight because of environmental factors such as those relating to diet or lifestyle. In the present embodiment, different configurations of the computer model 302 can be defined to represent different underlying conditions giving rise to a given phenotype of a biological system. Alternatively, or in conjunction, different configurations of the computer model 302 can be defined to represent different phenotypes of the biological system.

For certain applications, various configurations of the computer model 302 may be referred to as virtual patients, virtual organs, virtual tissues, or virtual cells. For instance, configurations X 306, Y 308, and Z 310 may correspond to virtual patients X, Y, and Z, respectively. A virtual patient can be defined to represent a patient (e.g., a real-world patient) having a given phenotype (e.g., a disease phenotype) based on a particular combination of underlying conditions. Various virtual patients can be defined to represent patients having the same phenotype but based on different underlying conditions. Alternatively, or in conjunction, various virtual patients can be defined to represent patients having different phenotypes. As another example, configurations X 306, Y 308, and Z 310 may correspond to virtual cells X, Y, and Z, respectively, where each virtual cell can be defined to represent a cell (e.g., a real-world cell) having a given phenotype based on a particular combination of underlying conditions.

In the present embodiment of the invention, a configuration (e.g., the configuration X 306) of the computer model 302 can be associated with a distinct set of values for the parameters of the computer model 302. Thus, configuration X 306 may be associated with a first set of parameter values, and configuration Y 308 may be associated with a second set of parameter values that differs in some fashion from the first set of parameter values. For instance, the second set of parameter values may include at least one parameter value differing from a corresponding parameter value included in the first set of parameter values. In a similar manner, configuration Z 310 may be associated with a third set of parameter values that differs in some fashion from the first and second set of parameter values.

For certain applications, one or more configurations of the computer model 302 can be created based on a baseline configuration that is associated with baseline parameter values. A different configuration can be created based on the baseline configuration by introducing a modification to the baseline configuration. Such modification can include, for example, a parametric change (e.g., altering or specifying one or more baseline parameter values), altering or specifying behavior of one or more variables, altering or specifying one or more functions representing interactions among variables, or a combination thereof. For instance, once the baseline configuration is defined, other configurations may be created based on the baseline configuration by starting with the baseline parameter values and altering one or more of the baseline parameter values. Alternative parameter values can be defined as, for example, disclosed in U.S. Pat. No. 6,078,739 discussed previously. These alternative parameter values can be grouped into different sets of parameter values that can be used to define different configurations of the computer model 302. For certain applications, the baseline configuration itself can be created based on another configuration (e.g., a different baseline configuration) in a manner as discussed above.

By way of example, if the modeled system represented by the computer model 302 is a biological system, the computer model 302 can include parameters that correlate to level of insulin resistance, nutrient composition of diet (e.g., fat composition of diet), level of pre-absorptive signaling, level of post-absorptive signaling, and level of adipose signaling. Various configurations (e.g., virtual patients) of the computer model 302 may be defined that are associated with distinct sets of values for these parameters.

Figure 4:
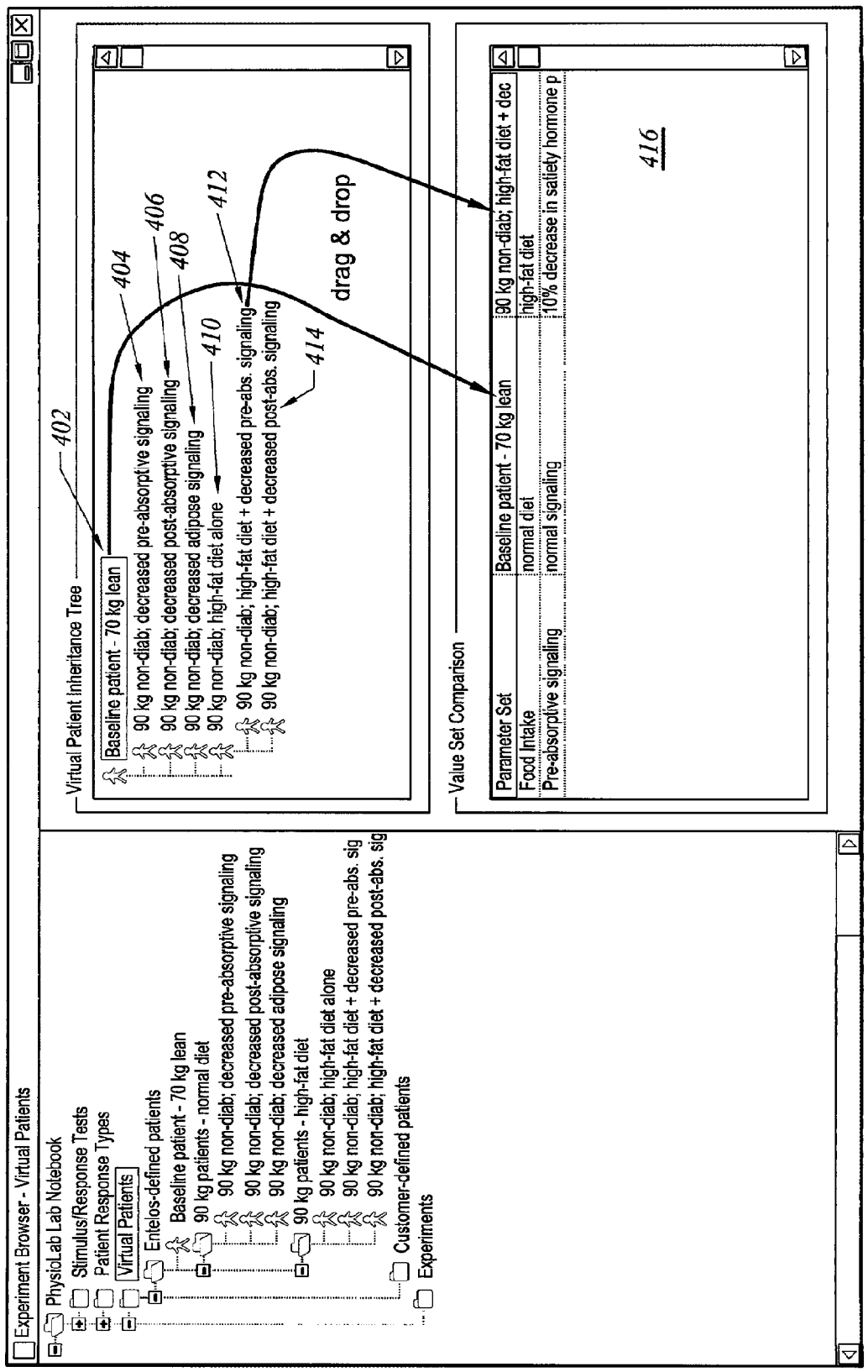
FIG. 4 illustrates an example of a user-interface screen that indicates various virtual patients that can be created based on a baseline virtual patient.

FIG. 4 illustrates an example of a user-interface screen that indicates various virtual patients that can be created based on a baseline virtual patient 402. Here, the baseline virtual patient 402 can be defined to represent a baseline patient (e.g., a healthy patient) and is associated with baseline parameter values that account for a normal level of insulin resistance (i.e., non-diabetic), a normal diet, a normal level of pre-absorptive signaling, a normal level of post-absorptive signaling, and a normal level of adipose signaling. Various virtual patients are created based on the baseline virtual patient 402 by altering one or more of the baseline parameter values to represent overweight patients having different underlying conditions.

As illustrated in FIG. 4, three virtual patients 404, 406, and 408 are created based on the baseline virtual patient 402 by altering one or more of the baseline parameter values to account for a decreased level of pre-absorptive signaling, a decreased level of post-absorptive signaling, and a decreased level of adipose signaling, respectively. For each of the virtual patients 404, 406, and 408, the decreased level of signaling corresponds to a genetic factor that gives rise to the overweight condition. As illustrated in FIG. 4, an additional virtual patient 410 is created based on the baseline virtual patient 402 by altering one or more of the baseline parameter values to account for a high-fat diet. For the virtual patient 410, the high-fat diet corresponds to an environmental factor that gives rise to the overweight condition. Two further virtual patients 412 and 414 are created based on the virtual patient 410 by altering one or more parameter values associated with the virtual patient 410 to account for a decreased level of pre-absorptive signaling and a decreased level of post-absorptive signaling, respectively. For each of the virtual patients 412 and 414, a combination of an environmental factor and a genetic factor gives rise to the overweight condition.

FIG. 4 also illustrates that two or more virtual patients can be compared to one another based on their parameter values. This can be accomplished, for example, by dragging and dropping selected virtual patients, individually or collectively, into the "Value Set Comparison" window 416. In the present example, the baseline virtual patient 402 and the virtual patient 412 are selected. As shown in FIG. 4, the baseline virtual patient 402 and the virtual patient 412 differ in their parameter values related to food intake and pre-absorptive signaling. If desired, various parameter values for one or more of the selected virtual patients can be indicated in the "Value Set Comparison" window 416 or in a separate window.

For certain applications, one or more configurations of the computer model 302 can be created based on a baseline configuration using linked simulation operations as, for example, disclosed in the co-pending and co-owned patent application to Paterson et al., entitled "Method and Apparatus for Conducting Linked Simulation Operations Utilizing A Computer-Based System Model", U.S. application Ser. No. 09/814,536, filed Mar. 21, 2001, the disclosure of which is incorporated herein by reference in its entirety. This application discloses a method for performing additional simulation operations based on an initial simulation operation where, for example, a modification to the initial simulation operation at one or more times is introduced. In the present embodiment of the invention, such additional simulation operations can be used to create additional configurations of the computer model 302 based on a baseline configuration that is created using the initial simulation operation. If desired, one or more simulation operations may be executed for a time sufficient to create one or more "stable" configurations of the computer model 302. Typically, a "stable" configuration is characterized by one or more variables under or substantially approaching equilibrium or steady-state condition.

Figure 5:
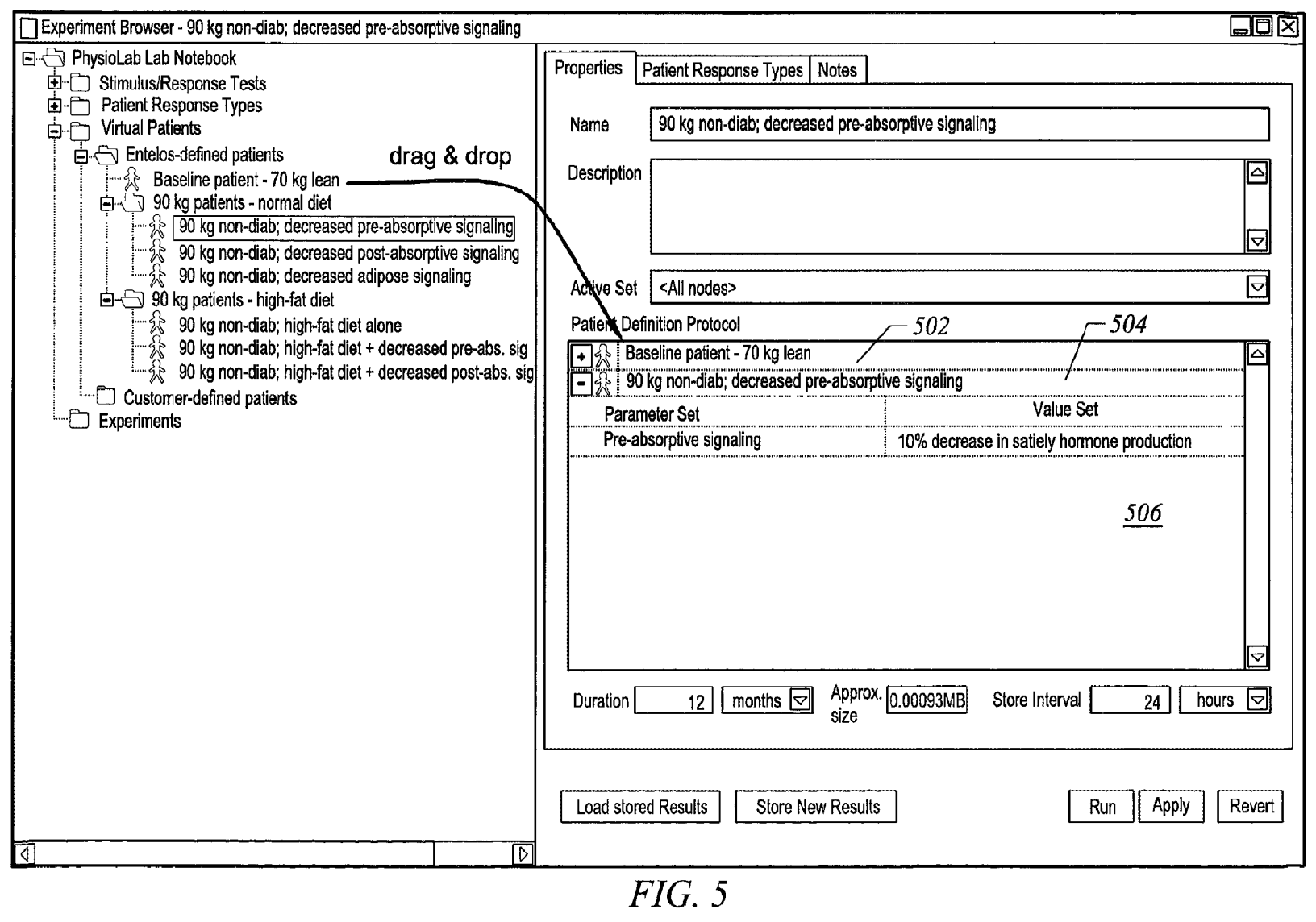

FIG. 5 illustrates an example of a user-interface screen indicating a virtual patient 504 that is created based on a baseline virtual patient 502. In this example, the virtual patient 504 labeled as "90 kg non-diab; decreased pre-absorptive signalling" is created from the baseline virtual patient 502 labeled as "Baseline patient –70 kg lean". Here, the baseline virtual patient 502 can be defined to represent a baseline patient (e.g., a healthy patient), while the virtual patient 504 created from the baseline virtual patient 502 can be defined to represent an overweight patient having a decreased level of pre-absorptive signaling. In the present example, the baseline virtual patient 502 can be dragged and dropped into the "Patient Definition Protocol" window 506, and the virtual patient 504 can be created based on this baseline virtual patient 502 in accordance with the method disclosed in U.S. application Ser. No. 09/814,536. As indicated in the "Patient Definition Protocol" window 506, parameter values related to level of pre-absorptive signaling can be specified for a simulation operation to create the virtual patient 504. As shown in FIG. 5, a name and description for the virtual patient 504 can be entered by a user.

It should be recognized that the methods described above, based on U.S. Pat. No. 6,078,739 and U.S. application Ser. No. 09/814,536, to create configurations of the computer model 302 are provided by way of example, and various configurations of the computer model 302 can be created by a variety of other methods that may be used alternatively, or in conjunction, with the methods described above.

For instance, various configurations can be created to represent different portions of the modeled system, such that the behavior of different portions of the modeled system can be simulated. A portion of the modeled system may be defined structurally, functionally, or both. By way of example, a portion of a biological system may be defined structurally as including an inter-cellular constituent, cellular constituent, or intra-cellular constituent that make up the biological system. Alternatively, or in conjunction, a portion may be defined functionally as including one or more biological processes associated with the biological system. For certain applications, one or more mathematical relations of the computer model 302 can be identified as being associated with a given portion of the modeled system, and a configuration can be defined to represent the given portion by, for example, specifying one or more boundary conditions for the one or more mathematical relations. The one or more boundary conditions may enable the behavior of one or more variables associated with the one or more mathematical relations to be simulated substantially independently of other variables. For instance, a boundary condition can specify the behavior of one or more of the other variables in a time-invariant manner (e.g., as a constant) or a time-varying manner (e.g., a stepwise manner or a periodic manner).

Validation Structure

Figure 6:
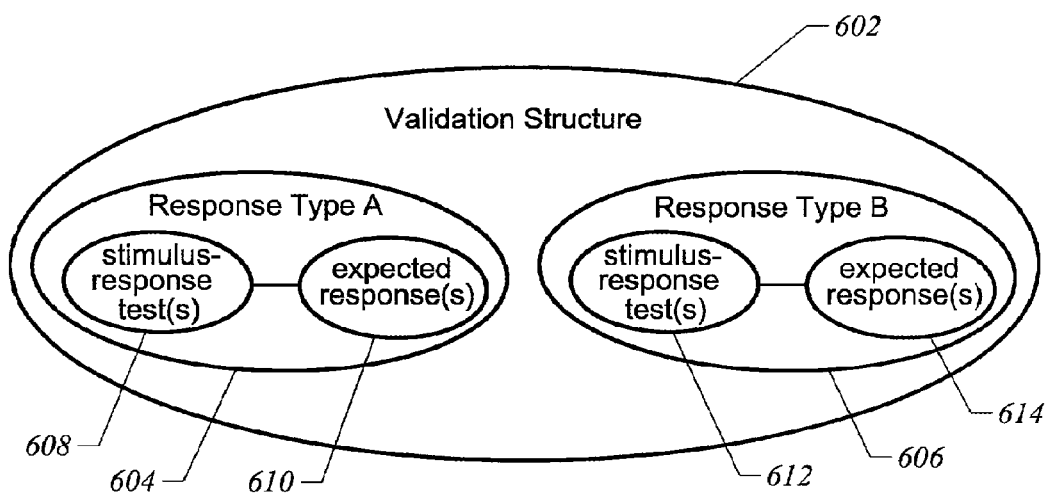
FIG. 6 illustrates the architecture of a validation structure that can be used to validate a computer model in accordance with an embodiment of the invention.

FIG. 6 illustrates the architecture of a validation structure 602 that can be used to validate a computer model (e.g., the computer model 302) in accordance with an embodiment of the invention. The validation structure 602 includes one or more stimulus-response tests. As shown in FIG. 6, the validation structure 602 includes a set of stimulus-response tests 608 and a set of stimulus-response tests 612. While two sets of stimulus-response tests are shown in FIG. 6, it should be recognized that more or less sets of stimulus-response tests can be used depending on the specific application.

A stimulus-response test can be defined to simulate a stimulus or perturbation that can be applied to a modeled system. Different stimulus-response tests can simulate stimuli that differ in some fashion from one another. By way of example, if a computer model to be validated represents a biological system, a stimulus-response test can simulate a stimulus that can be applied to the biological system. Stimuli that can be applied to a biological system can include, for example, tests (e.g., medical tests) such as pancreatic clamps; gastric emptying; hypothalamic tests; infusions of glucose, insulin, glucagon, somatostatin, and FFA; intravenous glucose tolerance test; oral glucose tolerance test; and insulin secretion experiments demonstrating acute and steady state insulin response to plasma glucose. Additional examples of stimuli include tests relating to environmental changes such as those relating to feeding behavior (e.g., short-term fasting, long-term fasting, single meal per day, multiple meals per day, caloric preload prior to a meal, self-feeding until equilibrium weight is established, and diets with varying nutrient compositions) as well as those relating to changes in levels of physical activity or exercise. Further examples of stimuli that can be applied to a biological system include existing or hypothesized therapies or treatment regimens and exposure to existing or hypothesized disease precursors.

Figure 7:
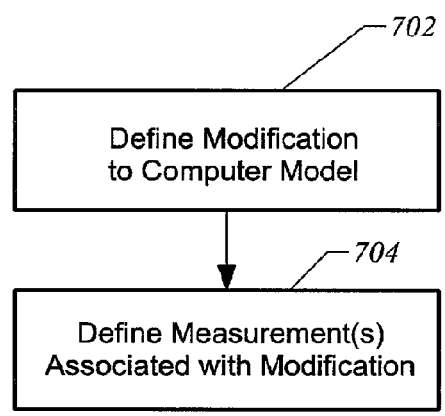
FIG. 7 illustrates a flow chart to create a stimulus-response test in accordance with an embodiment of the invention.

FIG. 7 illustrates a flow chart to create a stimulus-response test in accordance with an embodiment of the invention. The first step shown is to define a modification to a computer model (step 702). For certain applications, the stimulus-response test can define a modification to one or more configurations of the computer model to simulate a stimulus applied with respect to one or more model scenarios. By way of example, configurations of the computer model may include various virtual patients, and the stimulus-response test can define a modification to the various virtual patients to simulate a test that can be applied to various patients.

In the present embodiment of the invention, the stimulus-response test can be created by defining a modification to one or more processes represented by the computer model. More particularly, the stimulus-response test can be created by defining a modification to one or more mathematical relations included in the computer model, which one or more mathematical relations can represent one or more processes affected by a stimulus. A modification can include, for example, a parametric change (e.g., altering or specifying one or more parameter values), altering or specifying behavior of one or more variables, altering or specifying one or more functions representing interactions among variables, or a combination thereof. The stimulus-response test can define a modification that is to be introduced statically, dynamically, or a combination thereof, depending on the type of stimulus simulated by the stimulus-response test. For example, a modification can be introduced statically by replacing one or more parameter values with one or more modified parameter values that correlate to a stimulus. Alternatively, or in conjunction, a modification can be introduced dynamically to simulate a stimulus that is applied in a time-varying manner (e.g., a stepwise manner or a periodic manner). For instance, a modification can be introduced dynamically by altering or specifying parameter values at certain times or for a certain time duration.

Figure 8:
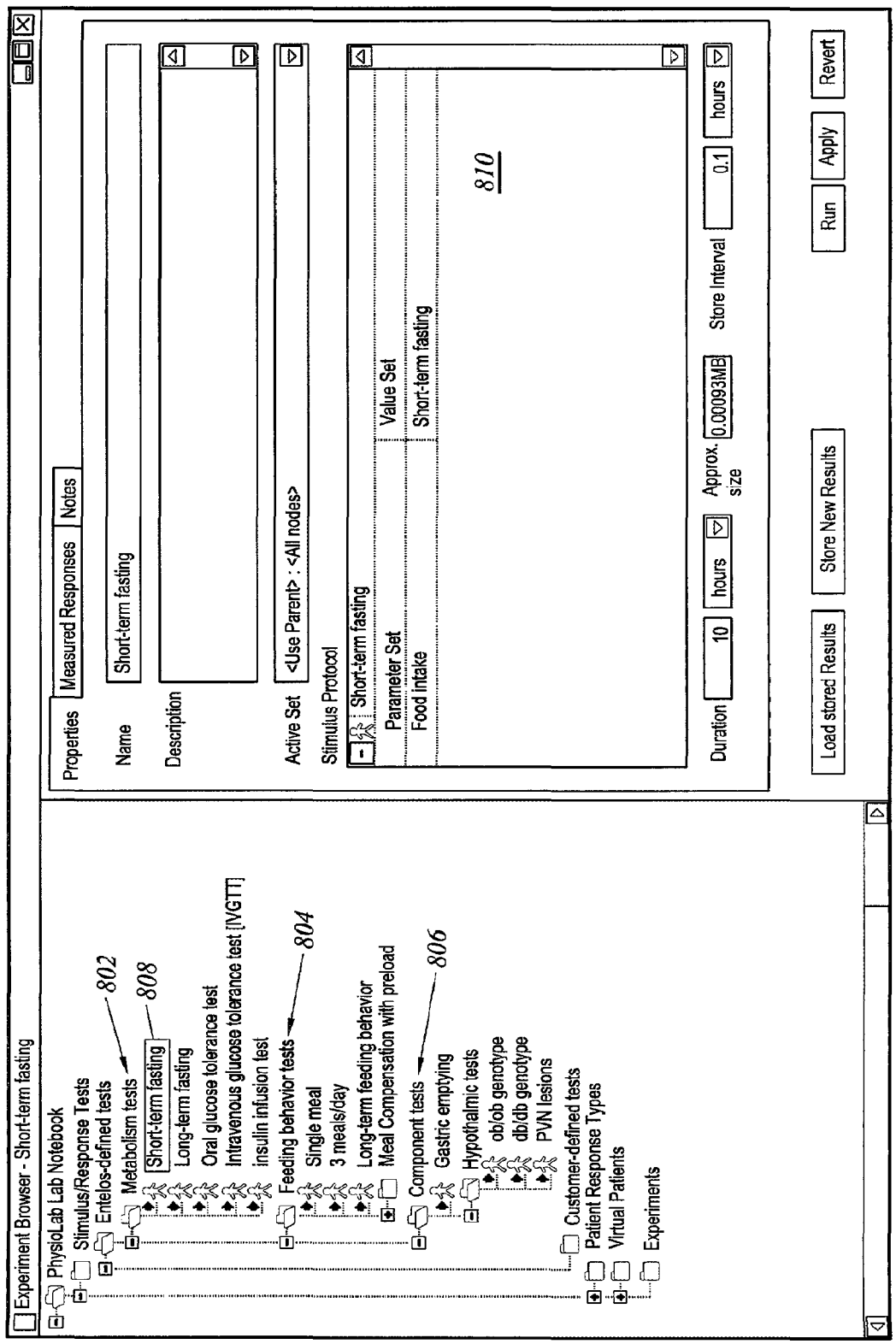
FIG. 8 illustrates an example of a user-interface screen that indicates various stimulus-response tests that can be created.

FIG. 8 illustrates an example of a user-interface screen indicating various stimulus-response tests that can be created. As shown in FIG. 8, various stimulus-response tests are indicated as being grouped under folders 802, 804, and 806 labeled as "Metabolism tests", "Feeding behavior tests", and "Component tests", respectively. In the present example, a stimulus-response test 808 labeled as "Short-term fasting" is created and can define a modification to one or more virtual patients to simulate short-term fasting. As indicated in the "Stimulus Protocol" window 810, the stimulus-response test 808 defines a modification with respect to parameter values related to food intake to simulate short-term fasting.

Turning back to FIG. 7, the next step shown is to define one or more measurements associated with the modification (step 704). In the present embodiment of the invention, a measurement can be defined such that a simulated response can be produced when the computer model is executed based on or in the presence of the modification. If multiple measurements are defined for a given stimulus-response test, a simulated response can be produced for each of the measurements. For certain applications, a measurement can be defined to correlate to a real-world measurement for a stimulus. By way of example, if the computer model represents a biological system, a measurement can be defined to correlate to an experimental or clinical measurement for a test that is applied to the biological system.

Typically, the definition of a measurement is based on one or more variables of the computer model or based on a function of one or more variables of the computer model. In the present embodiment of the invention, the definition of a measurement can be based on value of one or more variables or based on value of a function of one or more variables. For example, measurements can include a value at one or more times; an absolute or relative increase in a value over a time interval; an absolute or relative decrease in a value over a time interval; average value; minimum value; maximum value; time at minimum value; time at maximum value; area below a curve when values are plotted along a given axis (e.g., time); area above a curve when values are plotted along a given axis (e.g., time); pattern or trend associated with a curve when values are plotted along a given axis (e.g., time); rate of change of a value; average rate of change of a value; curvature associated with a value; number of instances a value exceeds, reaches, or falls below another value (e.g., a predefined value) over a time interval; minimum difference between a value and another value (e.g., a predefined value) over a time interval; maximum difference between a value and another value (e.g., a predefined value) over a time interval; a scaled value; a statistical measure associated with a value; as well as measurements based on combinations, aggregate representations, or relationships of two or more values (e.g., values of two or more different variables).

Figure 9:
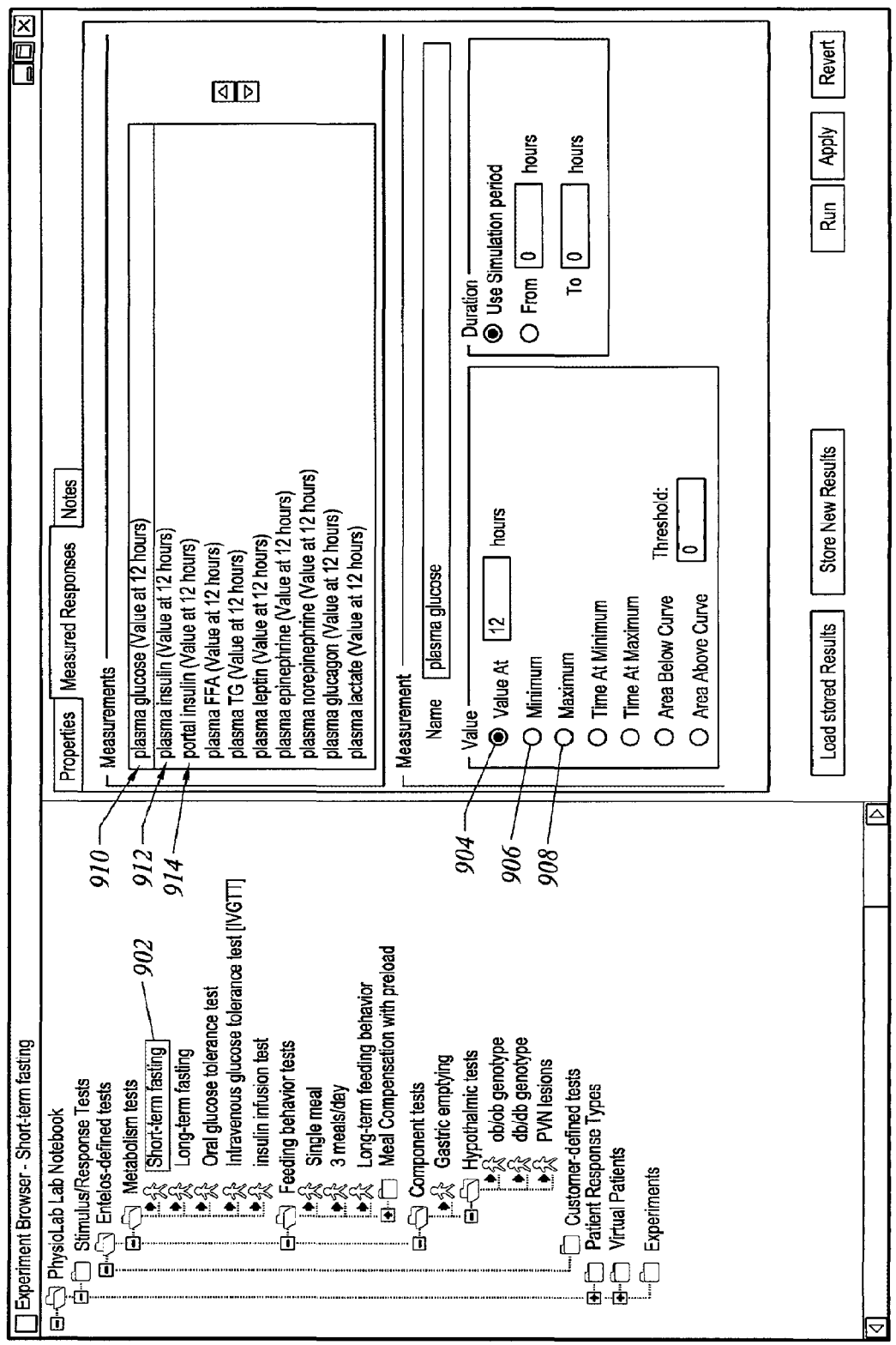
FIG. 9 illustrates an example of a user-interface screen that indicates how a measurement can be defined for a stimulus-response test.

FIG. 9 illustrates an example of a user-interface screen that indicates how a measurement can be defined for a stimulus-response test 902. In the present example, the stimulus-response test 902 labeled as "Short-term fasting" can be assigned one or more measurements. As shown in FIG. 9, various measurements (e.g., measurements 910, 912, and 914 labeled as "plasma glucose (Value at 12 hours)", "plasma insulin (Value at 12 hours)", and "portal insulin (Value at 12 hours)", respectively) can be defined for the stimulus-response test 902. A name for a measurement can be entered in order to link the measurement to one or more variables of a computer model. In the present example, the measurement 910 is linked to a variable that represents the level of plasma glucose. As shown in FIG. 9, various options (e.g., value 904, minimum 906, maximum 908, and so forth) are indicated, such that a simulated response can be produced based on a variable to which a measurement is linked. One or more of these options can be established by default or selected in accordance with a user-specified selection. In the present example, the option 904 is selected, and the measurement 910 is defined as the value of the variable representing the level of plasma glucose at 12 hours. As shown in FIG. 9, a time interval can be specified for a measurement. For instance, a measurement may be defined as the maximum of a variable during a particular time interval (e.g., from 1 hour to 2 hours).

For certain applications, a stimulus-response test can be defined to simulate a stimulus that is applied to a portion of a modeled system to evaluate the behavior of a section of a computer model representing the portion. As discussed previously, a portion of a modeled system may be defined structurally, functionally, or both. For certain applications, one or more mathematical relations of the computer model can be identified as being associated with a given portion of the modeled system, and a stimulus-response test can be defined to simulate a stimulus applied to the given portion by, for example, defining a modification and a measurement based on the one or more mathematical relations. Typically, the stimulus-response test will also specify one or more boundary conditions for the one or more mathematical relations, such that the behavior of one or more variables associated with the one or more mathematical relations can be simulated substantially independently of other variables. As discussed previously, a boundary condition can specify, for example, the behavior of one or more of the other variables in a time-invariant manner (e.g., as a constant) or a time-varying manner (e.g., a stepwise manner or a periodic manner).

A stimulus-response test can also define a preference for test updating. Test updating can entail, for example, reapplying the stimulus-response test to a computer model if the stimulus-response test is redefined (e.g., by changing a modification or measurement associated with the stimulus-response test), one or more configurations of the computer model is redefined (e.g., by altering one or more parameter values associated with a configuration), the computer model itself is redefined (e.g., by altering one or more mathematical relations included in the computer model), or a combination thereof. The preference for test updating can include various options such as, for example, automatically reapplying the stimulus-response test to one or more configurations (i.e., automatic test updating) and reapplying the stimulus-response test to one or more configurations upon receipt of a user-specified command (i.e., manual test updating). An option for a given stimulus-response test can be established by default or selected in accordance with a user-specified selection. Because certain stimulus-response tests (e.g., a stimulus-response test simulating self-feeding until equilibrium weight is established) may require a long simulation time, it may be desirable, but not required, that such stimulus-response tests be set up for manual test updating. On the other hand, other stimulus-response tests (e.g., a stimulus-response test simulating an oral glucose tolerance test) may require a relatively short simulation time and can be set up for automatic test updating.

With reference to FIG. 6, the validation structure 602 can also include one or more expected responses to one or more stimulus-response tests. As shown in FIG. 6, the validation structure 602 includes a set of expected responses 610 associated with the set of stimulus-response tests 608 and a set of expected responses 614 associated with the set of stimulus-response tests 612. If multiple measurements are defined for a given stimulus-response test, the stimulus-response test can be associated with an expected response for each of the measurements.

An expected response to a stimulus-response test can be based on actual, predicted, or desired behavior of a modeled system when subjected to a stimulus simulated by the stimulus-response test. The behavior of the modeled system can be, for example, an aggregate behavior of the modeled system or a portion of the modeled system when subjected to the stimulus. By way of example, if a computer model represents a biological system, an expected response to a stimulus-response test can be based on experimental or clinical behavior of the biological system when subjected to a test simulated by the stimulus-response test. For certain applications, an expected response to a stimulus-response test can include an expected range of behavior associated with a modeled system when subjected to a stimulus. Such range of behavior can arise, for example, as a result of variations of the modeled system having different intrinsic properties, different external influences, or both.

As shown in FIG. 6, the set of stimulus-response tests 608 and the set of expected responses 610 can be used to define a response type A 604, and the set of stimulus-response tests 612 and the set of expected responses 614 can be used to define a response type B 606. While two response types are shown in FIG. 6, it should be recognized that more or less response types can be defined depending on the specific application. Moreover, while response types A 604 and response type B 606 are each shown including a set of expected responses, it should be recognized that a given response type need not include a set of expected responses in all applications.

Selection and grouping of a set of stimulus-response tests and a set of expected responses to create a given response type can be guided by various considerations. Various logical or functional groupings of sets of stimulus-responses tests and sets of expected responses can be made to create various response types that can be used to validate a computer model. For certain applications, a response type can be defined to evaluate the similarity in behavior between one or more configurations of the computer model when subjected to a set of stimulus-response tests and a modeled system when subjected to a set of stimuli simulated by the set of stimulus-response tests. Provided sufficient similarity in behavior exists, one or more of the configurations can be validated and can be used for further analysis (e.g., predictive analysis).

If desired, various response types can be defined with respect to different variations of a modeled system having different intrinsic properties, different external influences, or both. For instance, response type A 604 can be defined with respect to a first variation of the modeled system, such that response type A 604 can be used to evaluate the similarity in behavior between one or more configurations of a computer model and the first variation of the modeled system. Also, response type B 606 can be defined with respect to a second variation of the modeled system, such that response type B 606 can be used to evaluate the similarity in behavior between one or more configurations of the computer model and the second variation of the modeled system.

Figure 10:
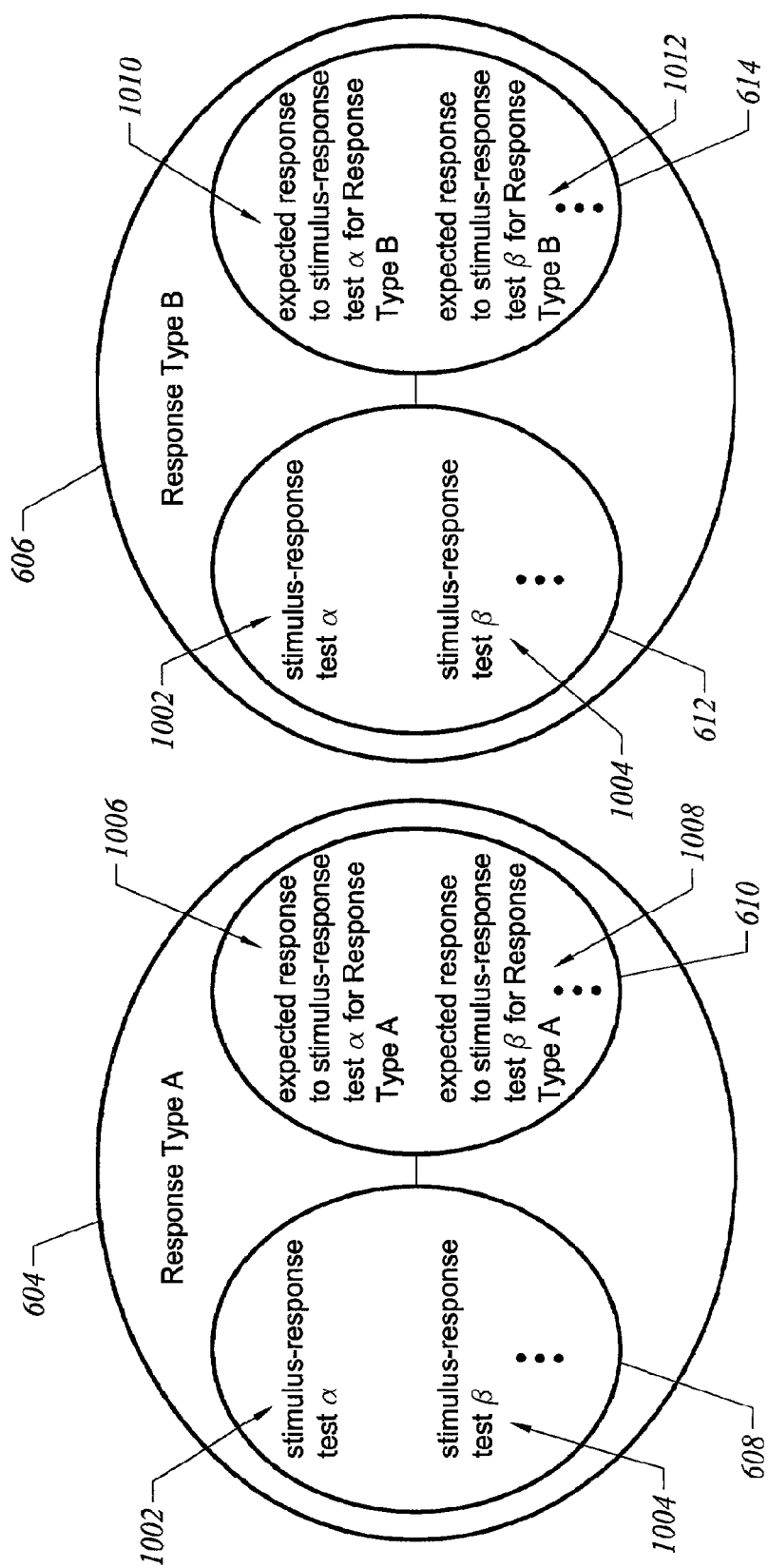
FIG. 10 illustrates an example of stimulus-response tests and expected responses that can be used to define various response types in accordance with an embodiment of the invention.

When subjected to the same stimulus, different variations of the modeled system can exhibit the same expected response or different expected responses. Accordingly, a stimulus-response test that simulates such stimulus can be created and can be used to define different response types while being associated with the same expected response or different expected responses. For instance, response type A 604 and response type B 606 can include one or more stimulus-response tests in common but can include different expected responses to each such stimulus-response test. FIG. 10 illustrates an example of stimulus-response tests and expected responses that can be used to define various response types (here, response type A 604 and response type B 606). In the present example, response type A 604 and response type B 606 both include a stimulus-response test α

1002 and a stimulus-response test β 1004. Response type A 604 includes expected responses 1006 and 1008 to the stimulus-response test α 1002 and the stimulus-response test β 1004, respectively, while response type B 606 includes expected responses 1010 and 1012 to the stimulus-response test α 1002 and the stimulus-response test β 1004, respectively. The expected responses 1006 and 1010 to the stimulus-response test α 1002 may be the same or different. Also, the expected responses 1008 and 1012 to the stimulus-response test β 1004 may be the same or different. While response type A 604 and response type B 606 are shown including two stimulus-response tests in common, it should be recognized that response type A 604 and response type B 606 can include more or less stimulus-response tests in common depending on the specific application.

By way of example, if one or more virtual patients are to be validated, a response type may be referred to as a patient response type. For instance, response type A 604 and response type B 606 may correspond to patient response type A and patient response type B, respectively. A patient response type can be defined with respect to a patient or group of patients of a particular type, such that the patient response type can be used to evaluate similarity in behavior between one or more virtual patients and the patient or group of patients of the particular type. In general, a patient or group of patients of a particular type can be any patient or any group of patients that responds to a set of stimuli simulated by a set of stimulus-response tests to exhibit a set of expected responses to the set of stimulus-response tests. For instance, patient response type A can be defined to evaluate the similarity in behavior between one or more virtual patients and a patient or group of patients that responds to a set of tests simulated by the set of stimulus-response tests 608 to exhibit the set of expected responses 610. In a similar manner, patient response type B can be defined to evaluate the similarity in behavior between one or more virtual patients and a patient or group of patients that responds to a set of tests simulated by the set of stimulus-response tests 612 to exhibit the set of expected responses 614.

For certain applications, a patient or group of patients of a particular type can correspond to a patient or group of patients of a particular phenotype (e.g., a particular disease phenotype), and a patient response type can be defined to evaluate the similarity in behavior between one or more virtual patients and the patient or group of patients of the particular phenotype. For instance, patient response type A can be defined with respect to a patient or group of patients of a first phenotype, and patient response type B can be defined with respect to a patient or group of patients of a second phenotype. It should be recognized that a patient response type can be defined with respect to a group of patients of the same phenotype but having different underlying conditions or with respect to a group of patients having different phenotypes, provided patients of such group exhibit sufficient commonality of behavior when subjected to a set of tests.

Figure 11:
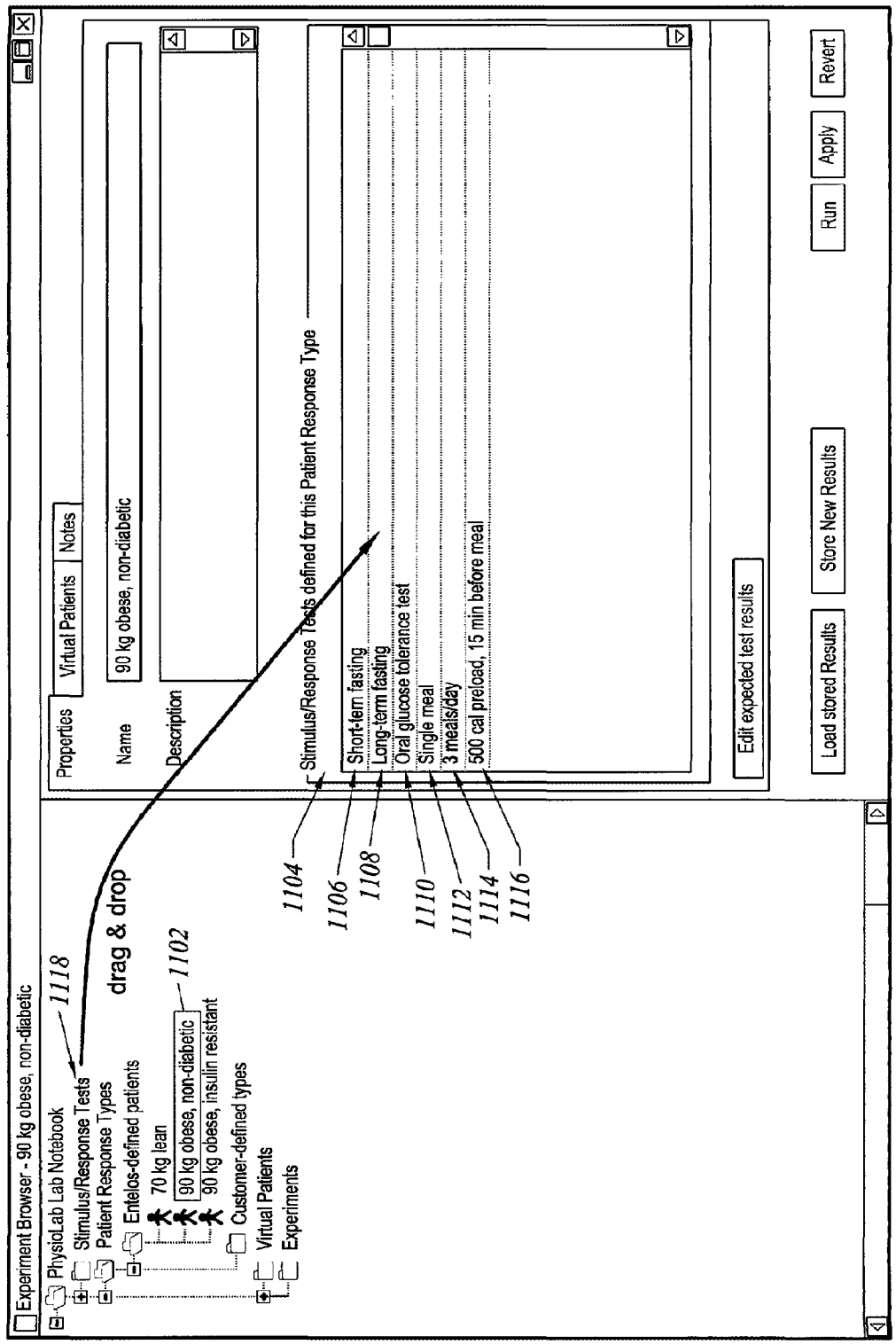
FIG. 11 illustrates an example of a user-interface screen indicating a patient response type that can be created using one or more stimulus-response tests.

FIG. 11 illustrates an example of a user-interface screen indicating a patient response type 1102 that can be created using one or more stimulus-response tests. In the present example, the patient response type 1102 is labeled as "90 kg obese, non-diabetic" and is defined with respect to an obese and non-diabetic patient or group of patients. This patient or group of patients may, for example, represent a significant market for a new obesity therapy. As shown in FIG. 11, various stimulus-response tests are associated with the patient response type 1102 by, for example, dragging and dropping the stimulus-response tests, individually or collectively, into the "Stimulus/Response Tests defined for this Patient Response Type" window 1104. In the present example, six stimulus-response tests 1106, 1108, 1110, 1112, 1114, and 1116 labeled as "Short-term fasting", "Long-term fasting", "Oral glucose tolerance test", "Single meal", "3 meals/day", and "500 cal preload, 15 min before meal", respectively, can be selected from the "Stimulus/Response Tests" folder 1118 and are associated with the patient response type 1102. The stimulus-response tests 1106, 1108, 1110, 1112, 1114, and 1116 can simulate tests that can be applied to the obese and non-diabetic patient or group of patients, and actual or predicted behavior for this patient or group of patients when subjected to these tests may be available. By associating the various stimulus-response tests 1106, 1108, 1110, 1112, 1114, and 1116 with the patient response type 1102, the behavior of one or more virtual patients can be evaluated relative to such actual or predicted behavior, and one or more virtual patients can be validated with respect to the patient response type 1102.

Using Validation Structure to Validate Computer Model

Figure 12:
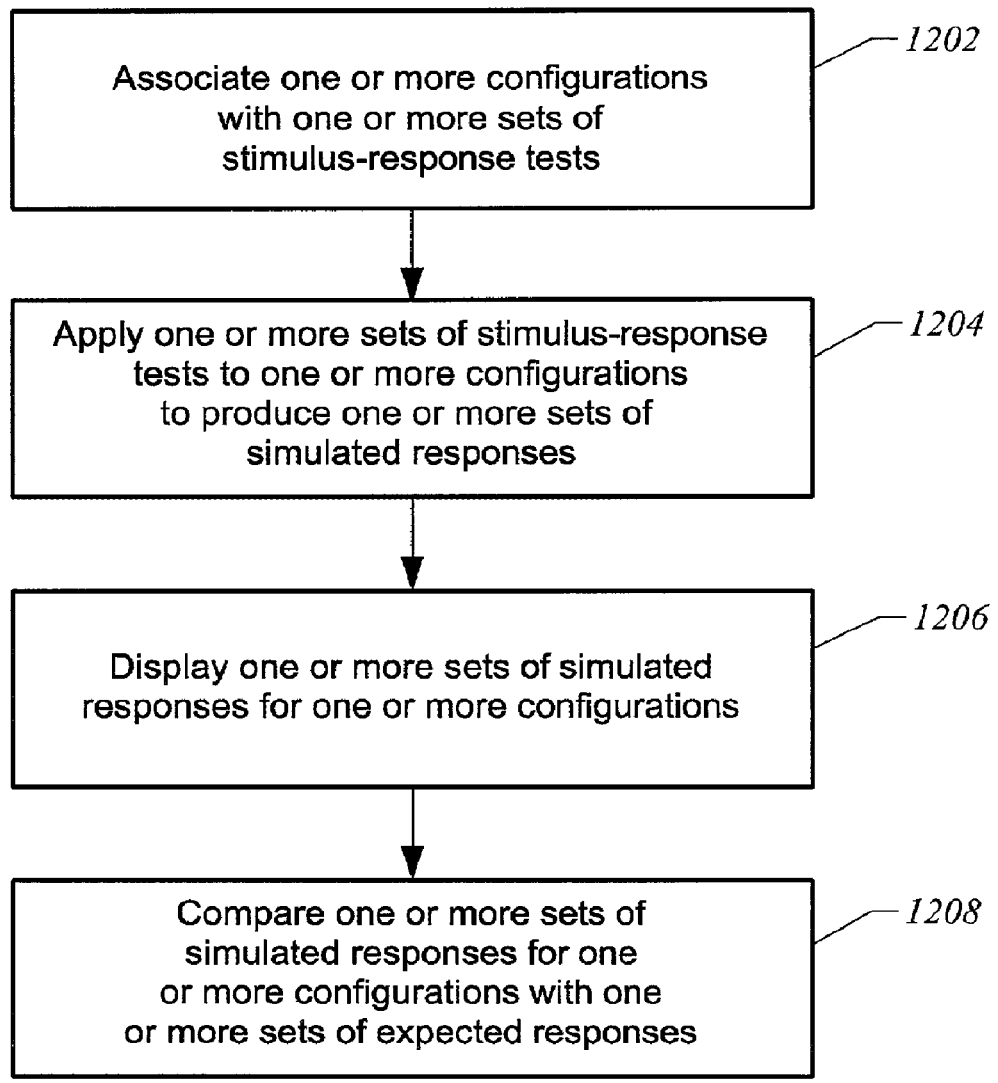
FIG. 12 illustrates a flow chart to validate a computer model using a validation structure, according to an embodiment of the invention.

Once a validation structure is defined, it can be used for the purpose of validating a computer model. FIG. 12 illustrates a flow chart to validate a computer model using a validation structure, according to an embodiment of the invention.

Figure 13:
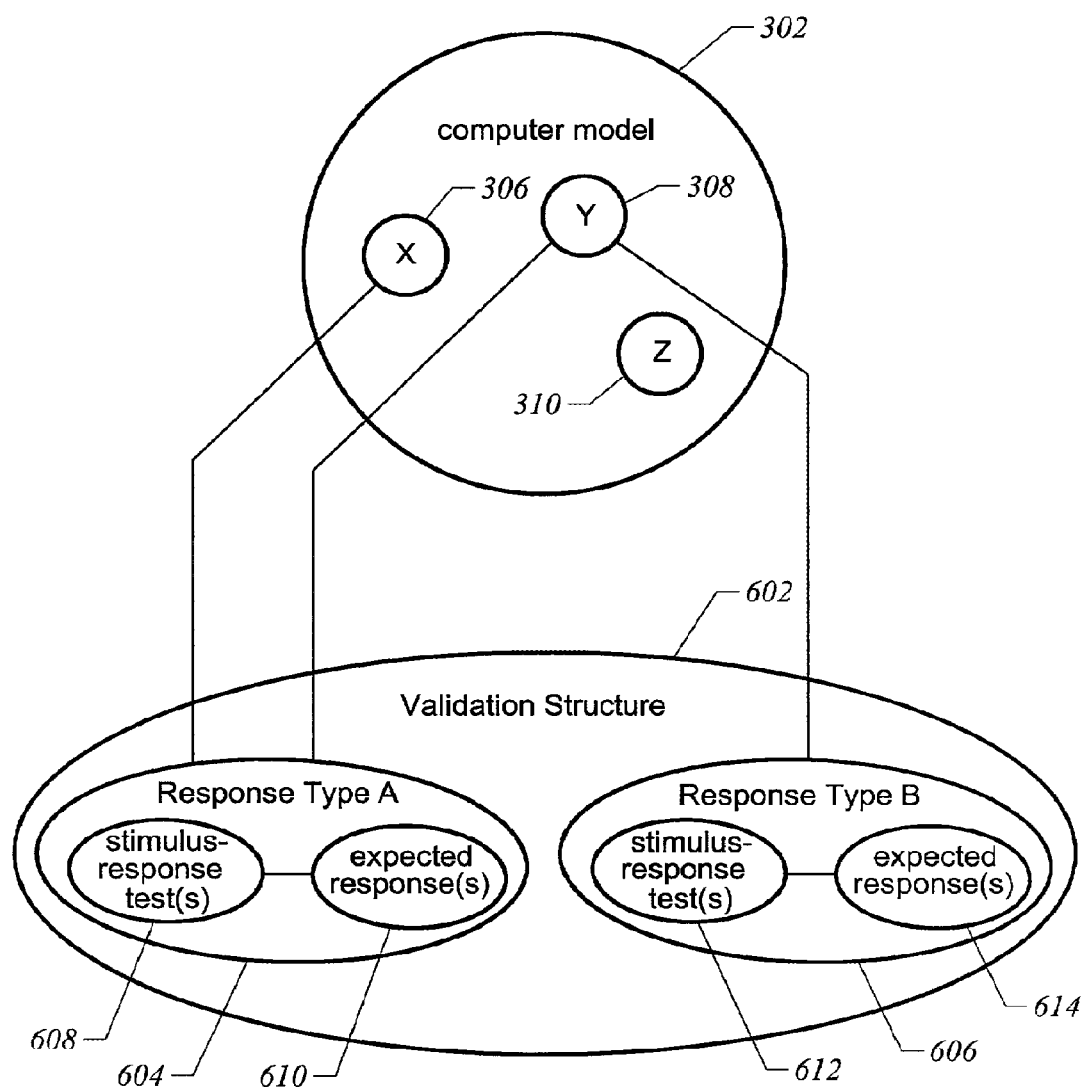
FIG. 13 illustrates associations between configurations of a computer model and response types of a validation structure in accordance with an embodiment of the invention.

The first step shown in FIG. 12 is to associate one or more configurations of the computer model with one or more sets of stimulus-response tests (step 1202). In the present embodiment of the invention, the validation structure includes one or more response types, and each response type can include a set of stimulus-response tests. Accordingly, the first step (step 1202) can entail associating one or more configurations of the computer model with one or more response types. Examples of associations between configurations of a computer model (here, the computer model 302) and response types of a validation structure (here, the validation structure 602) are illustrated in FIG. 13. As shown in FIG. 13, configuration X 306 is associated with response type A 604, while configuration Y 308 is associated with response type A 604 and response type B 606.

Figure 14:
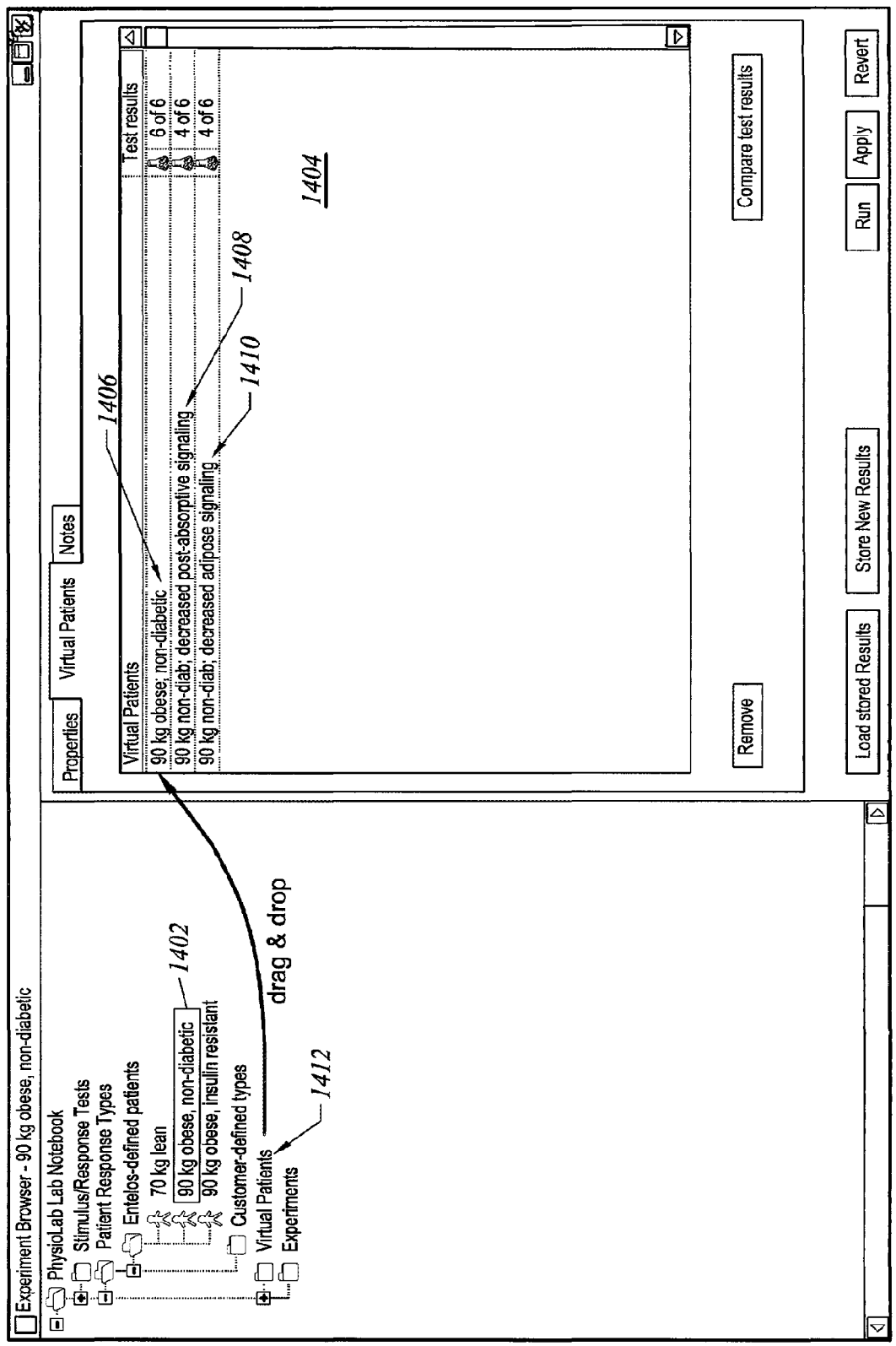
FIG. 14 illustrates an example of a user-interface screen indicating virtual patients that can be selected and associated with a given patient response type.

One or more configurations may be selected in accordance with a user-specified selection, and the one or more selected configurations can be associated with a given response type of the validation structure. FIG. 14 illustrates an example of a user-interface screen indicating various virtual patients that can be selected and associated with a patient response type 1402. Various virtual patients can be selected by, for example, dragging and dropping the virtual patients, individually or collectively, into the "Virtual Patients" window 1404 for the patient response type 1402. In the present example, three virtual patients 1406, 1408, and 1410 labeled as "90 kg obese, non-diabetic", "90 kg non-diab; decreased post-absorptive signalling", and "90 kg non-diab; decreased adipose signaling", respectively, can be selected from the "Virtual Patients" folder 1412 and are associated with the patient response type 1402 labeled as "90 kg obese, non-diabetic". By associating the various virtual patients 1406, 1408, and 1410 with the patient response type 1402, the behavior of the various virtual patients 1406, 1408, and 1410 can be evaluated such that one or more of the virtual patients 1406, 1408, and 1410 can be validated with respect to the patient response type 1402.

Figure 15:
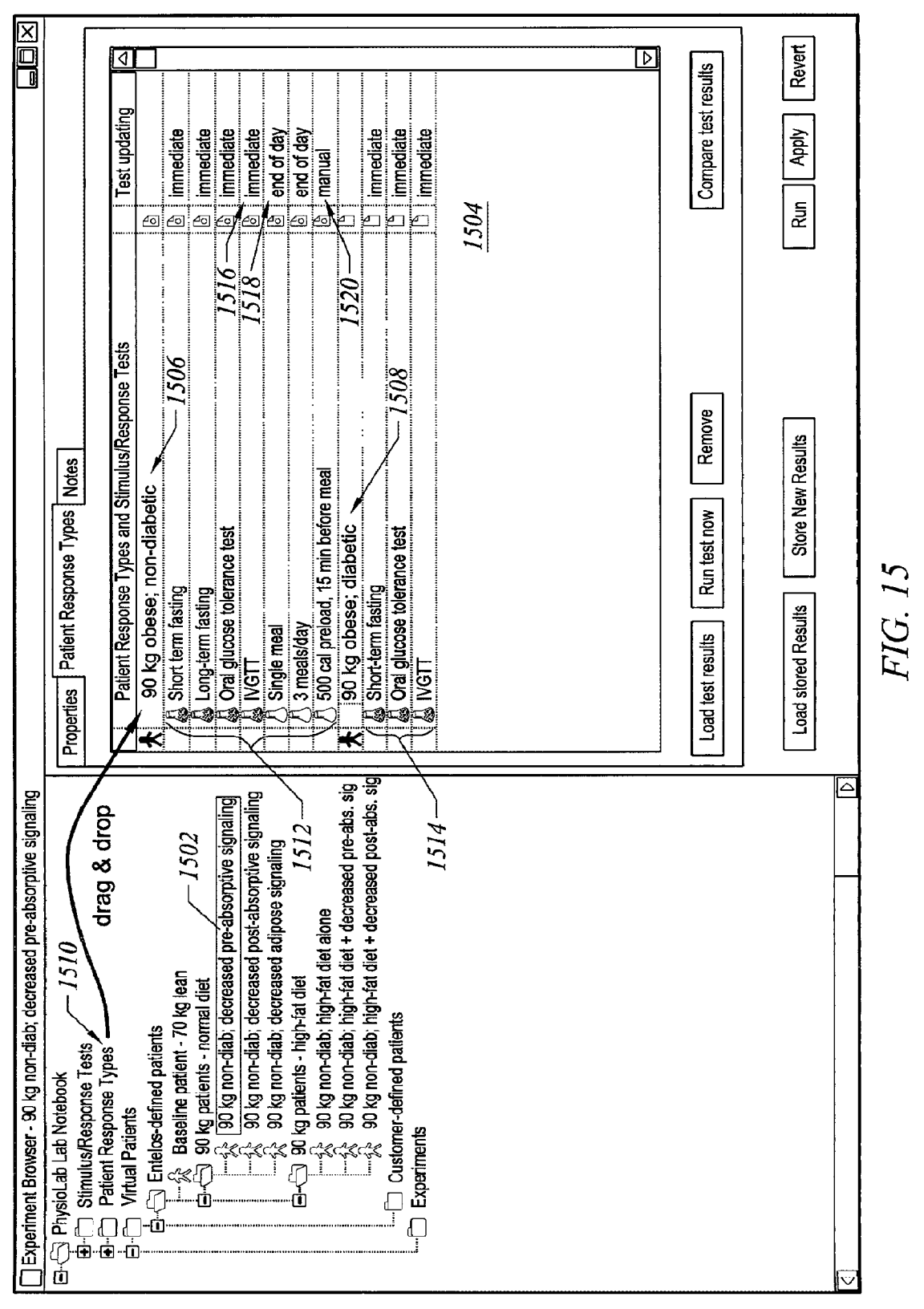

Alternatively, or in conjunction, one or more response types may be selected in accordance with a user-specified selection, and the one or more selected response types can be associated with a given configuration of the computer model. FIG. 15 illustrates an example of a user-interface screen indicating various patient response types that can be selected and associated with a virtual patient 1502. Various patient response types can be selected by, for example, dragging and dropping the patient response types, individually or collectively, into the "Patient Response Types and Stimulus/Response Tests" window 1504 for the virtual patient 1502. In the present example, patient response types 1506 and 1508 labeled as "90 kg obese; non-diabetic" and "90 kg obese; diabetic", respectively, can be selected from the "Patient Response Types" folder 1510 and are associated with the virtual patient 1502 labeled as "90 kg non-diab; decreased pre-absorptive signalling". By associating the various patient response types 1506 and 1508 with the virtual patient 1502, the behavior of the virtual patient 1502 can be evaluated such that the virtual patient 1502 can be validated with respect to one or more of the patient response types 1506 and 1508.

As shown in FIG. 15, each patient response type includes an associated set of stimulus-response tests 1512 or 1514. Indications (e.g., 1516, 1518, and 1520) are provided to represent preferences for test updating associated with the stimulus-response tests. In the present example, preferences for test updating include manual test updating as well as automatic test updating at various times (e.g., immediate or end of day).

Turning back to FIG. 12, the second step shown is to apply one or more sets of stimulus-response tests to one or more configurations of the computer model (step 1204). In the present embodiment of the invention, once an association between a configuration and a response type is made, a number of calculations can be made automatically to evaluate the behavior of the configuration when subjected to a set of stimulus-response tests associated with the response type. In particular, the configuration can be automatically executed based on the set of stimulus-response tests to produce a set of simulated responses for the configuration.

As discussed previously, a stimulus-response test can define a modification that can include, for example, a parametric change, altering or specifying behavior of one or more variables, altering or specifying one or more functions representing interactions among variables, or a combination thereof. In the present embodiment of the invention, various mathematical relations of the computer model, along with the modification introduced by the stimulus-response test, can be solved numerically by a computer using standard algorithms as, for example, disclosed in William H. Press et al. Numerical Recipes in C: The Art of Scientific Computing, 2nd edition (January 1993) Cambridge Univ. Press. For example, numerical integration of the ordinary differential equations defined previously can be performed to obtain values of variables at various times based on the modification. Such values of the variables can, in turn, be used to produce one or more simulated responses for one or more measurements defined for the stimulus-response test.

For certain applications, one or more stimulus-response tests can be applied to a configuration of the computer model using linked simulation operations as described in U.S. application Ser. No. 09/814,536 discussed previously. For instance, a configuration may be executed in accordance with an initial simulation operation, and, following introduction of a modification defined by a stimulus-response test, the configuration may be executed in accordance with one or more additional simulation operations that are linked to the initial simulation operation. By way of example, one or more stimulus-response tests associated with a patient response type can be applied to a virtual patient using the linked simulation operations described above.

If multiple configurations are associated with a given response type, a set of stimulus-response tests associated with the response type may be applied to the configurations simultaneously, sequentially, or a combination thereof. For instance, the set of stimulus-response tests can be initially applied to a first configuration to produce a set of simulated responses for the first configuration. Subsequently, the set of stimulus-response tests can be applied to a second configuration to produce a set of simulated responses for the second configuration. The set of stimulus-response tests can be sequentially applied to the configurations in accordance with an order that may be established by default or selected in accordance with a user-specified selection.

If multiple response types are associated with a given configuration, sets of stimulus-response tests associated with the response types may be applied to the configuration simultaneously, sequentially, or a combination thereof. For instance, a first set of stimulus-response tests associated with a first response type can be initially applied to the configuration to produce a first set of simulated responses for the configuration. Subsequently, a second set of stimulus-response tests associated with a second response type can be applied to the configuration to produce a second set of simulated responses for the configuration. The sets of stimulus-response tests can be sequentially applied to the configuration in accordance with an order that may be established by default or selected in accordance with a user-specified selection.

With reference to FIG. 12, the third step shown is to display one or more sets of simulated responses for one or more configurations of the computer model (step 1206). In the present embodiment of the invention, a set of simulated responses can be displayed for each association between a configuration and a response type. By displaying one or more sets of simulated responses, the behavior of one or more configurations can be evaluated, such that one or more configurations can be validated with respect to one or more response types. For certain applications, reports, tables, or graphs can be provided to facilitate understanding by a user.

Figure 16:
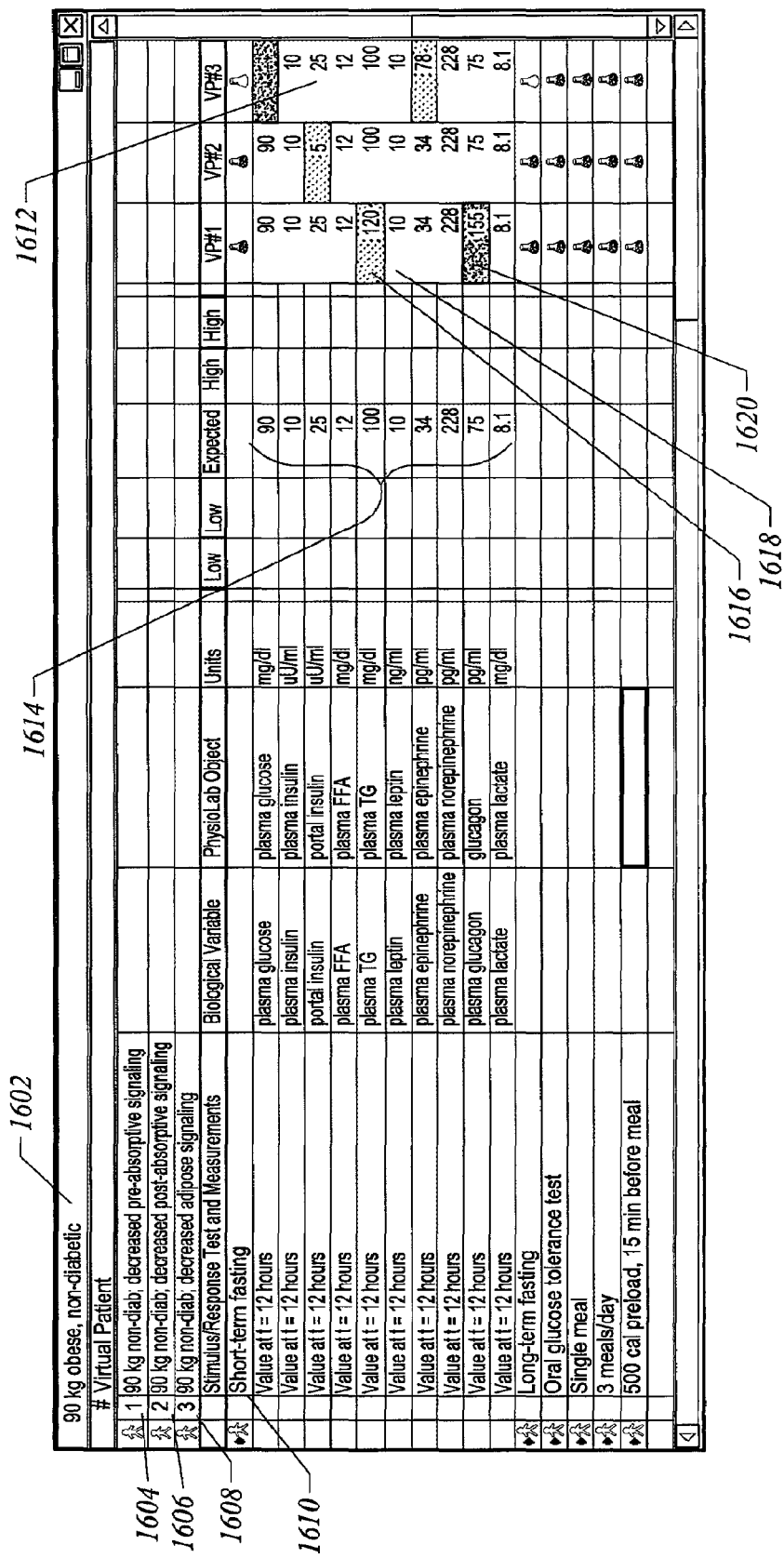
FIG. 16 illustrates an example of a user-interface screen that displays simulated responses for various virtual patients associated with a patient response type.

If multiple configurations are associated with a given response type, sets of simulated responses for two or more of the configurations can be displayed to allow comparative analysis. FIG. 16 illustrates an example of a user-interface screen that displays simulated responses for various virtual patients associated with a patient response type 1602. In the present example, three virtual patients 1604, 1606, and 1608 labeled as "90 kg non-diab; decreased pre-absorptive signalling", "90 kg non-diab; decreased post-absorptive signalling", and "90 kg non-diab; decreased adipose signalling", respectively, are associated with the patient response type 1602 labeled as "90 kg obese, non-diabetic". As shown in FIG. 16, various simulated responses (e.g., 1612) to a stimulus-response test 1610 labeled as "Short-term fasting" are displayed for each virtual patient. The simulated responses include values of various variables (e.g., variables representing levels of plasma glucose, plasma insulin, portal insulin, and so forth) for each virtual patient at 12 hours. While simulated responses for one stimulus-response test is displayed in FIG. 16, it should be recognized that simulated responses for one or more additional stimulus-response tests associated with the patient response type 1602 can be displayed as well.

If multiple response types are associated with a given configuration, sets of simulated responses for the configuration with respect to two or more of the response types can be displayed to allow comparative analysis. By way of example, a virtual patient can be associated with multiple patient response types, and sets of simulated responses for the virtual patient with respect to the multiple patient response types can be displayed. By displaying simulated responses with respect to multiple patient response types, the behavior of the virtual patient can be evaluated such that the virtual patient can be validated with respect to one or more of the patient response types.

In the present embodiment of the invention, one or more sets of expected responses included in one or more response types can be displayed. With reference to FIG. 16, the user-interface screen also displays expected responses 1614 to the stimulus-response test 1610. The expected responses 1614 include expected levels of plasma glucose, plasma insulin, portal insulin, and so forth at 12 hours and can be based on actual, expected, or desired data for a patient or group of patients associated with the patient response type 1602. By displaying the expected responses 1614, the simulated responses for the various virtual patients 1604, 1606, and 1608 can be evaluated relative to the expected responses 1614, such that one or more of the virtual patients 1604, 1606, and 1608 can be validated with respect to the patient response type 1602. While expected responses for one stimulus-response test is displayed in FIG. 16, it should be recognized that expected responses for one or more additional stimulus-response tests associated with the patient response type 1602 can be displayed as well.

Turning back to FIG. 12, the next step shown is to compare one or more sets of simulated responses for one or more configurations with one or more sets of expected responses (step 1208). In the present embodiment of the invention, for each association between a configuration and a response type, a set of simulated responses for the configuration can be compared with a set of expected responses associated with the response type.

For certain applications, comparing a set of simulated responses for a configuration with a set of expected responses associated with a response type can entail determining if a simulated response of the set of simulated responses is substantially consistent with an expected response of the set of expected responses. If a certain number (e.g., a majority or all) of the simulated responses of the set of simulated responses is substantially consistent with the set of expected responses, the configuration can be deemed to be validated with respect to the response type. It should be recognized that a simulated response can be substantially consistent with an expected response without being identical to the expected response. For instance, a simulated response can be substantially consistent with an expected response if the difference between the two responses lies within a certain range (e.g., within 20 percent or within 10 percent of the expected response). As another example, a simulated response can be substantially consistent with an expected response if the two responses exhibit relative changes that are similar but possibly with different absolute values. As a further example, an expected response can include an expected range of behavior, and a simulated response can be substantially consistent with the expected response if the simulated response lies within the expected range of behavior.

In the present embodiment of the invention, one or more indications can be provided based on comparing a set of simulated responses for a configuration with a set of expected responses associated with a response type. In particular, one or more validity indications can be provided to represent how closely the configuration's set of simulated responses approaches the set of expected responses for the response type. Validity indications can be provided, for example, in the form of colors, symbols, text messages, audio signals, or a combination thereof.

With reference to FIG. 16, various validity indications (e.g., 1616, 1618, and 1620) are provided that indicate how similarly or dissimilarly the various virtual patients 1604, 1606, and 1608 compare to a patient or group of patients associated with the patient response type 1602. In the present example, one or more ranges can be defined for each of the expected responses 1614 associated with the patient response type 1602, and a validity indication can be provided based on whether a simulated response for a virtual patient lies within the one or more ranges. A range for an expected response may be automatically defined based on the expected response or may be specified by a user. In the present example, an outer range and an inner range can be defined for each of the expected responses 1614, where the outer range includes the inner range. For example, an outer range and an inner range can be defined for the expected level of plasma glucose as 70 mg/dl to 110 mg/dl and 80 mg/dl to 100 mg/dl, respectively. As shown in FIG. 16, a first validity indication (e.g., 1618) of a first color or brightness level is provided to indicate that a simulated response for a virtual patient lies within or at boundaries of an inner range defined for an expected response. The first validity indication can be used to indicate that the simulated response is substantially consistent with the expected response. A second validity indication (e.g., 1616) of a second color or brightness level is provided to indicate that a simulated response for a virtual patient lies within or at boundaries of an outer range but outside of an inner range defined for an expected response. The second validity indication can be used to indicate a borderline situation that may merit further consideration by a user. A third validity indication (e.g., 1620) of a third color or brightness level is provided to indicate that a simulated response for a virtual patient lies outside an outer range defined for an expected response. The third validity indication can be used to indicate that the simulated response is not substantially consistent with the expected response. While three types of validity indications are shown in FIG. 16, it should be recognized that more or less types of validity indications can be used depending on the specific application.

For certain applications, a determination of whether a configuration is validated with respect to a response type can be made by a user by, for example, analyzing one or more validity indications. Alternatively, or in conjunction, the determination can be made automatically, and an indication can be provided based on comparing a set of simulated responses for the configuration with a set of expected responses associated with the response type to indicate whether the configuration is validated.

One or more configurations not deemed to be validated can be further manipulated in accordance with the present embodiment of the invention. For instance, a configuration that is not validated with respect to a given response type can be associated with one or more additional response types and processed as, for example, shown in FIG. 12 to evaluate the behavior of the configuration with respect to the one or more additional response types. Alternatively, or in conjunction, a configuration that is not validated with respect to a given response type can be redefined by, for example, altering one or more parameter values associated with the configuration. Once redefined, the configuration can be reprocessed with respect to the given response type in accordance with, for example, one or more of the steps shown in FIG. 12. If desired, the configuration can be further redefined and further reprocessed with respect to the given response type until a set of simulated responses for the configuration is substantially consistent with a set of expected responses associated with the given response type.

Using Validated Computer Model

Once a computer model has been validated, it can be used for a variety of applications. For instance, the validated computer model can be further evaluated to understand processes associated with a modeled system, to test hypothesis regarding the modeled system, or to predict behavior of the modeled system under varying conditions.

For certain applications, the behavior of one or more validated configurations of the computer model can be used for predictive analysis. For instance, a response type may be defined with respect to a variation of a modeled system, and one or more configurations validated with respect to the response type can be used to predict behavior of the variation of the modeled system when subjected to various stimuli.

By way of example, a patient response type may be defined with respect to a patient or group of patients of a particular type, and a virtual patient that has been validated with respect to the patient response type can be used to predict behavior of the patient or group of patients of the particular type. Virtual patients that have been validated with respect to different patient response types can be used to predict behavior of different patients or different groups of patients associated with the patient response types.

For certain applications, a virtual stimulus simulating a stimulus can be applied to a validated configuration in an attempt to predict how a real-world equivalent of the validated configuration would respond to the stimulus. In one embodiment, a virtual stimulus can be created in a manner similar to that used to create a stimulus-response test. Thus, a virtual stimulus can be created by, for example, defining a modification to one or more mathematical relations included in a computer model. The one or more mathematical relations can represent one or more processes affected by a stimulus simulated by the virtual stimulus. In addition, the virtual stimulus can define one or more measurements associated with the modification.

By way of example, once one or more virtual patients have been validated with respect to one or more patient response types, a variety of virtual stimuli can be defined to simulate existing or hypothesized therapies or treatment regimens or to simulate exposure to new disease precursors. A virtual stimulus can be applied to a validated virtual patient to produce a simulated response to the virtual stimulus, and the simulated response to the virtual stimulus can be used to predict behavior of a real-world equivalent of the virtual patient when subjected to a real-world equivalent of the virtual stimulus. For example, a virtual stimulus can be a virtual therapy that simulates the application of a new drug to predict its effectiveness on various patients. As another example, a virtual stimulus can simulate an exercise regimen to predict response of various overweight patients when subjected to the exercise regimen.

Each of the patent applications, patents, publications, and other published documents mentioned or referred to in this specification is herein incorporated by reference in its entirety, to the same extent as if each individual patent application, patent, publication, and other published document was specifically and individually indicated to be incorporated by reference.

While certain embodiments and examples have been described herein with reference to biological systems, it should be understood by one of ordinary skill in the art that embodiments of the invention are not limited to the life sciences field, and, specifically, are not limited to the ability to validate virtual patients.

An embodiment of the present invention relates to a computer storage product including a computer-readable medium having computer code thereon for performing various computer-implemented operations. The media and computer code may be those specially designed and constructed for the purposes of the present invention, or they may be of the kind well known and available to those having skill in the computer software arts. Examples of computer-readable media include, but are not limited to: magnetic media such as hard disks, floppy disks, and magnetic tape; optical media such as CD-ROMs and holographic devices; magneto-optical media such as floptical disks; and hardware devices that are specially configured to store and execute program code, such as application-specific integrated circuits ("ASICs"), programmable logic devices ("PLDs"), read only memories ("ROMs"), random access memories ("RAMs"), erasable programmable read only memories ("EPROMs"), and electrically erasable programmable read only memories ("EEPROMs"). Examples of computer code include machine code, such as produced by a compiler, and files containing higher level code that are executed by a computer using an interpreter. For example, an embodiment of the invention may be implemented using Java, C++, or other object-oriented programming language and development tools.

Moreover, an embodiment of the invention may be downloaded as a computer program product, where the program may be transferred from a remote computer (e.g., a server) to a requesting computer (e.g., a client) by way of data signals embodied in a carrier wave or other propagation medium via a communication link (e.g., a modem or network connection). Accordingly, as used herein, a carrier wave can be regarded as comprising a computer-readable medium.

Another embodiment of the invention may be implemented in hardwired circuitry in place of, or in combination with, machine-executable software instructions.

While the present invention has been described with reference to the specific embodiments thereof, it should be understood by those skilled in the art that various changes may be made and equivalents may be substituted without departing from the true spirit and scope of the invention as defined by the appended claims. In addition, many modifications may be made to adapt a particular situation, material, composition of matter, method, process step or steps, to the objective, spirit and scope of the present invention. All such modifications are intended to be within the scope of the claims appended hereto. In particular, while the methods disclosed herein have been described with reference to particular steps performed in a particular order, it will be understood that these steps may be combined, sub-divided, or re-ordered to form an equivalent method without departing from the teachings of the present invention. Accordingly, unless specifically indicated herein, the order and grouping of the steps is not a limitation of the present invention.

What is claimed is:

1. A computer-implemented method for validating multiple virtual patients, wherein the computer comprises a processor, a user-interface and a computer-readable medium, said method comprising:

receiving a baseline computer model of a biological system via the user-interface, wherein the computer model represents a plurality of biological processes of the biological system and wherein the computer model comprises a plurality of parameters;

the processor executing instructions encoded in the computer-readable medium, wherein the instructions comprise:

generating a plurality of virtual patients by changing at least one parameter of the plurality of parameters of the computer model, wherein each virtual patient is different from the other virtual patients by at least one parameter, but share the remaining parameters;

applying a validation structure to each virtual patient, wherein said validation structure comprises one or more sets of stimulus-response tests, wherein a stimulus-response test defines a modification to at least one biological process of the plurality of biological processes, and a set of expected responses associated with each stimulus-response test, wherein applying the validation structure comprises:

associating each virtual patient with one or more sets of stimulus response test;

applying one or more stimulus-response tests to each virtual patient to produce a simulated response for test for each of the plurality of virtual patients; and generating an indication of validity for each virtual patient by comparing the simulated response to the one of more stimulus-response tests with the associated expected response to the stimulus-response test for each virtual patient; and displaying the indication of validity for each virtual patient via the user-interface, wherein the indication of validity is selected from a first validity indication, a second validity indication and a third validity indication, wherein the first validity indication indicates that the simulated response is substantially consistent with the expected response, the second validity indication indicates a borderline situation that may merit further consideration by a user, and the third validity indication indicates that the simulated response lies outside an outer ramie defined for an expected response.

2. The computer-implemented method of claim 1, wherein the validation structure comprises one or more response types and generating the indication of validity further comprises comparing the simulated response to the one or more simulated response tests with a patient response type.

3. The computer-implemented method of claim 1, wherein the response type is associated with a phenotype.

4. The computer-implemented method of claim 1, wherein the expected response to the stimulus-response test is based on clinical or experimental behavior of the biological system when subjected to a test simulated by the stimulus-response test.

* * * * *